United States Patent

Hagen et al.

Patent Number: 5,486,618
Date of Patent: Jan. 23, 1996

[54] SUBSTITUTED 5-AMINOPYRAZOLES

[75] Inventors: Helmut Hagen, Frankenthal; Gerhard Nilz, Dannstadt-Schauerheim; Helmut Walter, Obrigheim; Andreas Landes, Limburgerhof, all of Germany

[73] Assignee: BASF Aktiengesellschaft, Ludwigsharen, Germany

[21] Appl. No.: 70,386

[22] PCT Filed: Dec. 3, 1991

[86] PCT No.: PCT/EP91/02286

§ 371 Date: Jun. 7, 1993

§ 102(e) Date: Jun. 7, 1993

[87] PCT Pub. No.: WO92/10480

PCT Pub. Date: Jun. 25, 1992

[30] Foreign Application Priority Data

Dec. 13, 1990 [DE] Germany ............. 40 39 733.5

[51] Int. Cl.⁶ ............................................. C07D 231/00
[52] U.S. Cl. ................................. 548/362.1; 548/356.1
[58] Field of Search .................. 514/404; 548/362.1, 548/356.1

[56] References Cited

U.S. PATENT DOCUMENTS

| | | | |
|---|---|---|---|
| 4,734,122 | 3/1988 | Gehring et al. | 548/362 |
| 4,808,623 | 2/1989 | Ooms et al. | 514/404 |

FOREIGN PATENT DOCUMENTS

| | | |
|---|---|---|
| 201852 | 11/1986 | European Pat. Off. |
| 235628 | 9/1987 | European Pat. Off. |
| 392241 | 10/1990 | European Pat. Off. |
| 418845 | 3/1991 | European Pat. Off. |

OTHER PUBLICATIONS

Chem Abst 115:49681 Jan. 30, 1991
Chem Abst 111: 57677 19889.
Synthesis of 5–Aminopyrazole–4–Carbonitriles, Dooley et al., Aust. J. Chem 1989, 42, 747–50.
J. Org. Chem. 21 (1956), 1240.
J. Heterocycl. Chem. 12 (1975), 1199.
Bull. Chem. Soc. Jpn. 60 (1987).

*Primary Examiner*—Paul J. Killos
*Attorney, Agent, or Firm*—Keil & Weinkauf

[57] ABSTRACT

Substituted 5-aminopyrazoles I

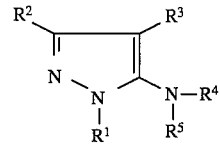

where $R^1$ is $C_1$–$C_8$-alkyl, $C_1$–$C_8$-hydroxyalkyl, phenyl which may carry 1–3 of the following radicals: halogen, nitro, alkyl, haloalkyl, alkoxy, haloalkoxy, alkylthio or —$NR^6R^7$, and which may additionally carry a number of halogen atoms so that the total number of radicals is 5, $R^6$ and $R^7$ are each H or $C_1$–$C_4$-alkyl, $R^2$ is H, $C_1$–$C_4$-alkyl or $C_1$–$C_4$-haloalkyl, $R^3$ is CN, —CO—$R^8$ or —CS—$R^8$, $R^8$ is OH, $C_1$–$C_4$-alkoxy, $NH_2$, $C_1$–$C_4$-alkylamino or di-$C_1$–$C_4$-alkylamino, $R^4$ and $R^5$ are each H, $C_1$–$C_4$-alkyl, $PX(OR^9)_2$, —$SO_2$—$R^9$, —$CX$—$R^{10}$, —$CX$—NH—$CY$—$R^9$ or $CX$—NH—$SO_2$—$R^{11}$, X and Y are each O or S, $R^9$ is one of the substituents $R^1$, $R^{10}$ is $C_1$–$C_{20}$-alkyl, $C_1$–$C_4$-alkoxy, unsubstituted or substituted phenyl or unsubstituted or substituted $NH_2$, $R^{11}$ is $NH_2$, $C_1$–$C_4$-alkylamino, di-$C_1$–$C_4$-alkylamino, pyrrolidinyl, piperidinyl or morpholinyl, $R^4$ and $R^5$ together form a group $=CR^{12}R^{13}$ or —CO—W—CO—, $R^{12}$ is H, $NH_2$, $C_1$–$C_4$-alkylamino or $C_3$–$C_8$-cycloalkylamino, $R^{13}$ is $NH_2$, $C_1$–$C_4$-alkylamino, di-$C_1$–$C_4$-alkylamino, $C_3$–$C_8$-cycloalkylamino, pyrrolidin-1-yl, piperidin-1-yl, morpholin-4-yl, unsubstituted or substituted phenyl or unsubstituted or substituted pyridyl and W is an unsubstituted or substituted ethylene or ethenylene bridge, an unsubstituted or substituted 5-membered or 6-membered 1,2-C-bonded aromatic or heteroaromatic bridge, or an unsubstituted or substituted 5-membered or 6-membered 1,2-C-bonded cycloalkylene or cycloalkenylene bridge, and the basic salts of the compounds I in which $R^3$ is hydroxycarbonyl or hydroxythiocarbonyl, and the acidic salts of the compounds I which contain a basic nitrogen atom, with the exception of 1-phenyl- and 1-methyl-4-cyano-5-acylaminopyrazole, 1-methyl-4-cyano-5-(chloromethylcarbonylamino)-pyrazole, 1-methyl-4-cyano-5-(phenylcarbonylamino)-pyrazole, 1-methyl-4-cyano-5-(p-chlorophenylcarbonylamino)-pyrazole and the compounds I in which $R^1$ is methyl, phenyl, 4-chlorophenyl or 4-nitrophenyl, $R^2$ is hydrogen, methyl or trifluoromethyl, $R^3$ is cyano and $R^4$ and $R^5$ are simultaneously hydrogen, and herbicides which contain 2-(4-hetaryloxy)- and 2-(4-aryloxy)-phenoxyacetic acid or -propionic acid derivatives and/or cyclohexenone derivatives as herbicidal active ingredients and substituted 5-aminopyrazoles I' or, in the case of acidic terminal groups or basic nitrogen atoms, the salts of I' as antidotes.

10 Claims, No Drawings

SUBSTITUTED 5-AMINOPYRAZOLES

The present invention relates to novel 5-aminopyrazoles of the general formula I

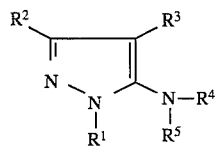

where
$R^1$ is $C_1$–$C_8$-alkyl, $C_1$–$C_8$-hydroxyalkyl may carry or a phenyl group which may carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio or —$NR^6R^7$, where $R^6$ and $R^7$ are each hydrogen or $C_1$–$C_4$-alkyl, and the phenyl group may additionally carry a further number of halogen atoms so that the total number of radicals is 4 or 5;

$R^2$ is hydrogen or $C_1$–$C_4$-alkyl which may be unsubstituted or partially or completely halogenated;

$R^3$ is cyano, CO—$R^8$ or CS—$R^8$, where $R^8$ is hydroxyl, $C_1$–$C_4$-alkoxy, amino, $C_1$–$C_4$-alkylamino or di-$C_1$–$C_4$-alkylamino;

$R^4$ and $R^5$ are each hydrogen, $C_1$–$C_4$-alkyl, $PX(OR^5)_2$, $SO_2$—$R^9$, CX—$R^{10}$, CX—NH—CY—$R^9$ or CX—NH—$SO_2$—$R^{11}$, where
X and Y are each oxygen or sulfur;
$R^9$ is one of the substituents $R^1$;
$R^{10}$ is $C_1$–$C_{20}$-alkyl, $C_1$–$C_4$-alkoxy or a phenyl group which may carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio or —$NR^6R^7$, and which may additionally carry a further number of halogen atoms so that the total number of radicals is 5; amino which may be unsubstituted or may carry a $C_1$–$C_4$-alkyl, cycloalkyl or phenyl radical, where the phenyl radical in turn may carry from one to three of the following radicals: halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio and the phenyl group may additionally contain a further number of halogen atoms so that the total number of radicals is 4 or 5;

$R^{11}$ is amino, $C_1$–$C_4$-alkylamino, di-$C_1$–$C_4$-alkylamino, pyrrolidinyl, piperidinyl or morpholinyl;
or
$R^4$ and $R^5$ together form a group $=CR^{12}R^{13}$ or —CO—W—CO—, where $R^{12}$ is hydrogen, amino, $C_1$–$C_4$-alkylamino or $C_3$–$C_8$-cycloalkylamino;

$R^{13}$ is amino, $C_1$–$C_4$-alkylamino, di-$C_1$–$C_4$-alkylamino, $C_3$–$C_8$-cycloalkylamino, pyrrolidin-1-yl, piperidin-1-yl, morpholin-4-yl, phenyl or pyridyl, where the two last-mentioned substituents may furthermore carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio;

W is an ethylene or ethenylene bridge, a 5-membered or 6-membered 1,2-C-bonded aromatic or heteroaromatic bridge having a nitrogen, oxygen or sulfur atom as hetero atom, where these bridge members may furthermore carry, on each substitutable carbon atom, a radical selected from up to 2 of the following: halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio and partially or completely halogenated $C_1$–$C_4$-alkylthio, and where the bridge members may additionally carry a number of halogen atoms equivalent to the number of further substitutable carbon atoms, or a 5-membered or 6-membered 1,2-C-bonded cycloalkylene or cycloalkenylene bridge, where these substituents may furthermore carry from one to four of the following radicals: halogen or $C_1$–$C_4$-alkyl;

and the basic salts of the compounds I in which $R^3$ is hydroxycarbonyl or hydroxythiocarbonyl and the acidic salts of the compounds I which contain a basic nitrogen atom, with the exception of 1-phenyl- and 1-methyl-4-cyano-5-acylaminopyrazole, 1-methyl-4-cyano-5-(chloromethylcarbonylamino)-pyrazole, 1-methyl-4-cyano-5-(phenylcarbonylamino)-pyrazole, 1-methyl-4-cyano-5-(p-chlorophenylcarbonylamino)-pyrazole, and the compounds I in which $R^1$ was methyl, phenyl, 4-chlorophenyl or 4-nitrophenyl, $R^2$ was hydrogen, methyl or trifluoromethyl, $R^3$ was cyano and $R^4$ and $R^5$ were simultaneously hydrogen.

The present invention furthermore relates to a process for the preparation of the compounds I and to herbicides containing one or more herbicidal active ingredients from the group consisting of A) the 2-(4-hetaryloxy)- or 2-(4-aryloxy)-phenoxyacetic acid derivatives of the formula X

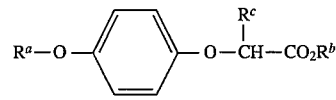

where
$R^a$ is phenyl, pyridyl, benzoxazyl, benzothiazyl or benzopyrazinyl, where these aromatic ring systems may carry up to two of the following radicals: halogen, nitro, $C_1$–$C_4$-alkyl, partially or completely halogenated $C_1$–$C_4$-alkyl and/or partially or completely halogenated $C_1$–$C_4$-alkoxy;
$R^b$ is hydrogen, $C_1$–$C_5$-alkyl, $C_3$–$C_5$-alkylideneimino, $C_3$–$C_5$-alkylideneiminooxy-$C_2$- or $C_3$-alkyl or one equivalent of a plant-tolerated cation and
$R^c$ is hydrogen or methyl,
and
B) the cyclohexenone derivates of the formula XI

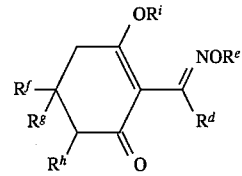

where
$R^d$ is $C_1$–$C_4$-alkyl;
$R^e$ is $C_1$–$C_4$-alkyl, $C_3$- or $C_4$-alkenyl, $C_3$- or $C_4$-alkynyl or partially or completely halogenated $C_3$- or $C_4$-alkenyl;
a $C_1$–$C_4$-alkylene or $C_2$–$C_4$-alkenyl chain, both of which may furthermore carry from one to 3 $C_1$–$C_3$-alkyl radicals and/or halogen atoms, or a 3-membered to 6-membered alkylene or 4-membered to 6-membered alkenylene chain which may be substituted by $C_1$–$C_3$-alkyl and each of which contains as a chain member an oxygen or sulfur atom not directly adjacent to the oxime ether moiety, all the abovementioned chains carrying on the terminal position the phenyl ring which in turn may be substituted by from one to three radicals selected from the group consisting of one benzyloxycarbonyl or phenyl radical and from one to three of the following radicals: nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl and $C_1$–$C_4$-alkoxycarbonyl, and it being possible for the phenyl ring furthermore to carry a number of halogen atoms such that the total number of radicals is 4 or 5;

thienylmethyl which may furthermore carry a halogen atom;

$R^f$ is $C_1$–$C_4$-alkyl which may be monosubstituted by $C_1$–$C_4$-alkylthio or by $C_1$–$C_4$-alkoxy;

a 5-membered or 6-membered saturated or monounsaturated ring system which, in addition to carbon members, may contain an oxygen or sulfur atom or a sulfinyl or sulfonyl group, where this ring may carry up to three of the following radicals: hydroxyl, halogen, $C_1$–$C_4$-alkyl, partially or completely halogenated $C_1$–$C_4$-alkyl, $C_1$–$C_4$-alkoxy and/or $C_1$–$C_4$-alkylthio;

a 10-membered saturated or monounsaturated heterocyclic structure which contains two oxygen atoms or sulfur atoms and may be substituted by up to three $C_1$–$C_4$-alkyl groups and/or methoxy groups;

phenyl or pyridyl, where these groups may carry up to three of the following radicals: $C_1$–$C_4$-alkyl, partially or completely halogenated $C_1$–$C_4$-alkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and/or benzoylamino;

pyrrolyl, pyrazolyl, thiazolyl or isoxazolyl, each of which may carry a $C_1$–$C_4$-alkyl group;

$R^g$ is hydrogen or hydroxyl or, when $R^f$ is $C_1$–$C_6$-alkyl, is $C_1$–$C_6$-alkyl;

$R^h$ is hydrogen, cyano, halogen, $C_1$–$C_4$-alkoxycarbonyl or a group

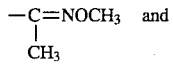 and $R^i$ is hydrogen or one equivalent of an environmentally compatible cation, and one or more antagonistic substituted 5-aminopyrazoles of the formula I', where I' has the same meaning as I without the exception, or a basic salt of the compounds I' in which $R^3$ is hydroxycarbonyl or hydroxythiocarbonyl, or an acidic salt of the compounds I' which carry a basic nitrogen atom.

The present invention furthermore relates to methods for selectively controlling undesirable plant growth with these herbicides.

Aust. J. Chem. 42 (1989), 747 discloses 1-methyl- and 1-phenyl-substituted 5-amino-4-cyanopyrazoles, and J. Org. Chem. 21 (1956), 1240 discloses 1-alkyl- and 1-aryl-substituted 5-amino-4-cyanopyrazoles and 1-alkyl- and 1-aryl-substituted 5-amino-4-pyrazolecarboxamides of the same type as the compounds I.

5-Amino-4-pyrazolecarboxamides of the same type as compounds I, having different radicals in the 1- and/or 3-positions, are described in J. Heterocycl. Chem. 12 (1975), 1199.

The compounds known from the literature serve as intermediates.

Furthermore, Bull. Chem. Soc. Jpn. 60 (1987), 4480 discloses 5-amino-4-cyano-1-phenyl-3-trifluoromethylpyrazole and 5-amino-4-cyano-1-(p-nitrophenyl)-3-trifluoromethylpyrazole as byproducts.

According to EP-A 201 852, EP-A 235 628 and EP-A 392 241, 5-amino-1-arylpyrazoles which carry an alkylthio, alkylsulfinyl or alkylsulfonyl radical in the 4-position have insecticidal, acaricidal and nematicidal activity.

Finally, EP-A 418 845 discloses pharmaceutically active 1-(het)arylpyrazoles which by definition may carry, inter alia, an alkylamino group.

An antidote effect of the known 5-aminopyrazoles in combination with herbicidal active ingredients is not mentioned in the stated publications.

It was an object of the present invention to provide compounds which, when the abovementioned herbicides of the formulae X and XI are used, reduce disadvantages at least to such an extent that the yield of the crops at harvest is no longer reduced or not reduced significantly.

We have found that this object is achieved by the substituted 5-aminopyrazoles I defined at the outset.

We have also found processes for the preparation of the compounds I and methods for the combined treatment of crops on the one hand with the antidote compounds I or I', where I' has the same meaning as I without the exception, and, on the other hand, with the herbicides X and/or XI, whether the herbicidal active ingredient and the antidote compound are formulated and applied together or separately and, in the case of separate application, the order in which the herbicidal active ingredient and the antidote are applied being unimportant.

Derivatives I and I' having acidic terminal groups or having basic nitrogen atoms may be in the form of their agriculturally useful salts.

Suitable acid addition salts are the salts of acids which do not adversely affect the antidote activity of I, for example the hydrochlorides, hydrobromides, sulfates, nitrates, phosphates, oxalates or dodecylbenzenesulfonates.

Suitable basic salts are the salts of bases which do not adversely affect the antidote activity of I, for example the alkali metal salts, in particular the sodium and potassium salts, the alkaline earth metal salts, in particular calcium, magnesium and barium salts, transition metal salts, in particular manganese, copper, zinc and iron salts, ammonium salts which may carry from one to three $C_1$–$C_4$-alkyl or hydroxy-$C_1$–$C_4$-alkyl substituents and/or a phenyl or benzyl substituent, in particular diisopropylammonium, tetramethylammonium, tetrabutylammonium, trimethylbenzylammonium and trimethyl-(2-hydroxyethyl)-ammonium salts, the phosphonium salts, the sulfonium salts, in particular tri-$C_1$–$C_4$-alkylsulfonium salts, and the sulfoxonium salts, in particular tri-$C_1$–$C_4$-alkylsulfoxonium salts.

The substituents in the novel compounds I have the following specific meanings:

$R^1$ is branched or straight-chain $C_1$–$C_8$-alkyl, in particular $C_1$–$C_4$-alkyl, such as methyl, ethyl, n-propyl, isopropyl, n-butyl, isobutyl or tert-butyl, particularly preferably methyl;

$C_1$–$C_8$-hydroxyalkyl, in particular $C_1$–$C_4$-hydroxyalkyl, such as hydroxymethyl, 2-hydroxyethyl, 3-hydroxypropyl or 4-hydroxybutyl;

phenyl which may furthermore carry from one to three of the following radicals:

halogen, such as fluorine, chlorine, bromine or iodine, in particular fluorine or chlorine, nitro, $C_1$–$C_4$-alkyl as stated above, partially or completely halogenated $C_1$–$C_4$-alkyl, such as fluoromethyl, difluoromethyl, trifluoromethyl, chloromethyl, trichloromethyl, bromomethyl, pentafluoroethyl or 2-chloro-1,1,2-trifluoroethyl, $C_1$–$C_4$-alkoxy, such as methoxy, ethoxy, n-propoxy, isopropoxy, n-butoxy or tert-butoxy, partially or completely halogenated $C_1$–$C_4$-alkoxy, such as fluoromethoxy, difluoromethoxy, trifluoromethoxy, chloromethoxy, dichloromethoxy or trichloromethoxy, $C_1$–$C_4$-alkylthio, such as methylthio, ethylthio, n-propylthio, isopropylthio, n-butylthio or tert-butylthio, preferably methylthio or ethylthio, or —$NR^6R^7$, where $R^6$ and $R^7$ are each hydrogen or $C_1$–$C_4$-alkyl as stated above, and where the phenyl group may additionally contain a number of halogen atoms so that the total number of radicals is 4 or 5, particularly preferably phenyl or 4-chlorophenyl;

$R^1$ is very particularly preferably methyl or phenyl;

$R^2$ is hydrogen;

$C_1$–$C_4$-alkyl as stated above;

partially or completely halogenated $C_1$–$C_4$-alkyl as stated above;

$R^2$ is particularly preferably hydrogen;

$R^3$ is cyano;

CO—$R^8$ or CS—$R^8$, where $R^8$ is hydroxyl, $C_1$–$C_4$-alkoxy as stated above, in particular methoxy or ethoxy, amino, $C_1$–$C_4$-alkylamino, such as methylamino, ethylamino, n-propylamino, isopropylamino, n-butylamino or tert-butylamino, in particular methylamino or ethylamino, or di-$C_1$–$C_4$-alkylamino, such as dimethylamino, diethylamino, methylethylamino, or methyl-n-butylamino;

$R^3$ is very particularly preferably cyano;

$R^4$ and $R^5$ are each hydrogen;

$C_1$–$C_4$-alkyl as stated above;

$PX(OR^9)_2$, $SO_2$—$R^9$, CX—$R^{10}$, CX—NH—CY—$R^9$ or CX—NH—$SO_2$—$R^1$, where X and Y are each oxygen or sulfur;

$R^9$ is one of the substituents $R^1$;

$R^{10}$ is branched or straight-chain $C_1$–$C_{20}$-alkyl, in particular $C_1$–$C_6$-alkyl as stated above, $C_1$–$C_4$-alkoxy as stated above, phenyl which may furthermore carry from one to three of the following radicals: halogen as stated above, in particular fluorine or chlorine, nitro, $C_1$–$C_4$-alkyl as stated above, in particular methyl, partially or completely halogenated $C_1$–$C_4$-alkyl as stated above, in particular trifluoromethyl, $C_1$–$C_4$-alkoxy as stated above, in particular methoxy, partially or completely halogenated $C_1$–$C_4$-alkoxy as stated above, in particular methoxy or ethoxy, $C_1$–$C_4$-alkylthio as stated above, in particular methylthio, or —$NR^6R^7$ as stated above, and the phenyl group may additionally carry a number of halogen atoms as stated above, in particular fluorine or chlorine, so that the total number of radicals is 4 or 5;

amino which may be unsubstituted or may carry a $C_1$–$C_4$-alkyl radical as stated above, in particular methyl or ethyl, a $C_3$–$C_8$-cycloalkyl radical, such as cyclopropyl, cyclobutyl, cyclopentyl, cyclohexyl, cycloheptyl or cyclooctyl, in particular cyclopropyl, cyclopentyl or cyclohexyl, or a phenyl radical, which in turn may carry from one to three of the following radicals: halogen as stated above, in particular fluorine or chlorine, $C_1$–$C_4$-alkyl as stated above, partially or completely halogenated $C_1$–$C_4$-alkyl as stated above, in particular trifluoromethyl or trichloromethyl, $C_1$–$C_4$-alkoxy as stated above, in particular methoxy or ethoxy, partially or completely halogenated $C_1$–$C_4$-alkoxy as stated above, in particular trifluoromethoxy or trichloromethoxy, or $C_1$–$C_4$-alkylthio as stated above, in particular methylthio or ethylthio, and the phenyl radical may additionally carry a number of halogen atoms as stated above, in particular fluorine or chlorine so that the total number of radicals is 4 or 5;

$R^{11}$ is amino, $C_1$–$C_4$-alkylamino as stated above, in particular methylamino or ethylamino, di-$C_1$–$C_4$-alkylamino as stated above, in particular dimethylamino or diethylamino, pyrrolidin-1-yl, piperidin-1-yl, piperazin-1-yl or morpholin-4-yl, where the heterocyclic radicals may carry one or two $C_1$–$C_4$-alkyl groups as stated above;

or $R^4$ and $R^5$ together form a group =$CR^{12}R^{13}$ or —CO—W—CO—, where $R^{12}$ is hydrogen, amino, $C_1$–$C_4$-alkylamino as as stated above, in particular methylamino or ethylamino, $C_3$–$C_8$-cycloalkylamino, such as cyclopropylamino, cyclobutylamino, cyclopentylamino, cyclohexylamino, cycloheptylamino or cyclooctylamino, in particular cyclopropylamino, cyclopentylamino or cyclohexylamino;

$R^{13}$ is hydrogen, amino, $C_1$–$C_4$-alkylamino as stated above, in particular methylamino or ethylamino, di-$C_1$–$C_4$-alkylamino as stated above, in particular dimethylamino or diethylamino, $C_3$–$C_8$-cycloalkylamino as stated above, in particular cyclopropylamino, cyclopentylamino or cyclohexylamino;

pyrrolidin-1-yl, piperidin-1-yl, morpholin-4-yl, phenyl or pyridyl, where the two last-mentioned substituents may carry from one to three of the following radicals: halogen as stated above, in particular fluorine or chlorine, nitro, $C_1$–$C_4$-alkyl as stated above, in particular methyl, ethyl, isopropyl or tert-butyl, partially or completely halogenated $C_1$–$C_4$-alkyl as stated above, in particular trifluoromethyl, $C_1$–$C_4$-alkoxy as stated above, in particular methoxy or ethoxy, partially or completely halogenated $C_1$–$C_4$-alkoxy as stated above, in particular trifluoromethoxy and/or $C_1$–$C_4$-alkylthio as stated above, in particular methylthio, particularly preferably phenyl or pyrid-2-yl;

W is an ethylene or ethenylene bridge, a 5-membered or 6-membered 1,2-C-bonded aromatic or heteroaromatic bridge having a nitrogen, oxygen or sulfur atom as the hetero atom, where these bridge members may furthermore carry, on each substitutable carbon atom, a radical selected from up to 2 of the following: halogen as stated above, in particular fluorine or chlorine, $C_1$–$C_4$-alkyl as stated above, in particular methyl or tert-butyl, partially or completely halogenated $C_1$–$C_4$-alkyl as stated above, in particular trifluoromethyl, $C_1$–$C_4$-alkoxy as stated above, in particular methoxy, partially or completely halogenated $C_1$–$C_4$-alkoxy as stated above, in particular trifluoromethoxy, $C_1$–$C_4$-alkylthio as stated above, in particular methylthio and/or partially or completely halogenated $C_1$–$C_4$-alkylthio, such as fluoromethylthio, chloromethylthio, bromomethylthio, trichloromethylthio, trifluoromethylthio or pentafluoroethylthio, in particular trifluoromethylthio, and where the bridge members may furthermore carry a number of halogen atoms as stated above, in particular fluorine or chlorine, equivalent to the number of further substitutable carbon atoms present in the aromatic moiety, particularly preferably

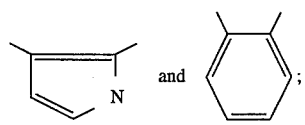

or a 5-membered or 6-membered 1,2-C-bonded cycloalkylene or cycloalkenylene bridge, such as cyclopentylidene, cyclohexylidene, cyclopentenylidene or cyclohexenylidene, where these substituents may furthermore carry from one to four halogen atoms as stated above, in particular fluorine or chlorine, and/or $C_1$–$C_4$-alkyl as stated above, in particular methyl,
particularly preferably

The substituted 5-aminopyrazoles of the formula I are obtainable by various methods, preferably by one of the following processes:

a) Reaction of alkoxycyanoalkenes II with hydrazines III to give 5-aminopyrazoles Ia, where $R^4$ and $R^5$ are each hydrogen:

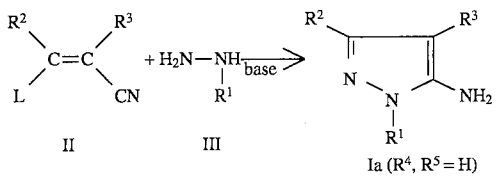

L is $C_1$–$C_4$-alkoxy.

The reaction is usually carried out in a conventional manner [cf. Robins et al., J. Org. Chem. 21 (1956), 1240] in an inert solvent or diluent, for example in an alcohol, such as methanol, ethanol, n-propanol or isopropanol, in an ether, such as dioxane or tetrahydrofuran, or in a polar aprotic solvent, such as dimethylformamide, dimethyl sulfoxide or N-methylpyrrolidone, or, with the use of a phase transfer catalyst, in a 2-phase system of water and a hydrocarbon, eg. carbon tetrachloride.

In the case of compounds having a lower reactivity, it is advisable to carry out the reaction in the presence of a strong organic or inorganic base.

Examples of suitable bases are alkali metal hydroxides, such as sodium hydroxide or potassium hydroxide, alkaline earth metal hydroxides, such as calcium hydroxide, alkali metal alcoholates, such as sodium methylate, sodium ethylate, potassium ethylate or potassium tert-butylate, alkaline earth metal alcoholates, such as calcium alcoholate, alkali metal hydrides, such as sodium hydride or potassium hydride, alkaline earth metal hydrides, such as calcium hydride, aliphatic amines, such as dimethylamine, triethylamine or triisopropylamine, dimethylaniline, dimethylbenzylamine, piperidine and heteroaromatic amines, such as pyridine or 4-dimethylaminopyridine.

In the case of the amines, the reaction can also be carried out in an excess of base in the absence of a solvent.

Examples of suitable phase transfer catalysts are trioctylpropylammonium chloride and cetyltrimethylammonium chloride [cf. Synthesis (1974), 867].

All reactants are advantageously used in stoichiometric amounts, but an excess of up to about 10 mol % of one or the other component may also be used.

If the base is used as a solvent, it is present in a relatively large excess.

In general, the reaction temperature is from 0° to 150° C. C preferably from 20° to 100° C. in particular the boiling point of the particular solvent.

The reaction is usually carried out at atmospheric pressure or at the autogenous pressure of the solvent used.

Further possible methods of synthesis comprise reacting acrylonitrile derivatives with arylhydrazines, the open-chain product then being oxidized with air or sodium hypochlorite and cyclized in the presence of a base (cf. EP-A 245 646);

acetonitrile derivatives and orthoformic esters with hydrazines II [cf. Dooley, Aust. J. Chem. 42 (1989), 747] and acetonitrile derivatives with hydrazonoyl bromides [cf. Tanaka et al., Bull. Chem. Soc. Jpn. 60 (1987), 4480].

b) Reaction of substituted 5-aminopyrazoles Ia with an electrophilic compound IV to IX:

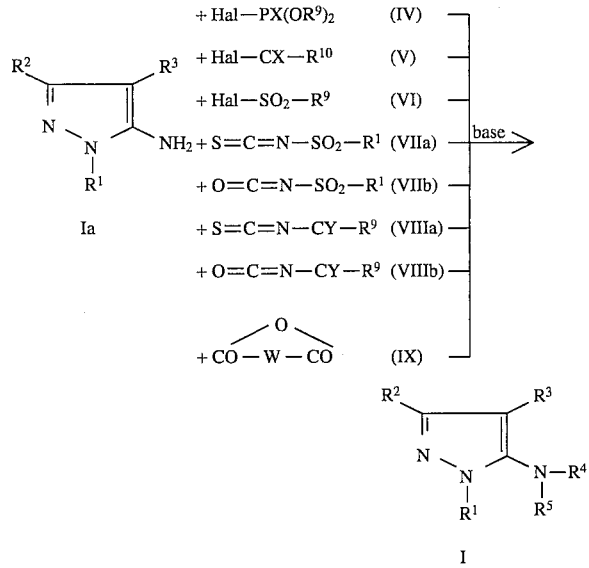

Hal is chlorine or bromine.

The reactions are usually carried out by a conventional process in an inert solvent or diluent in the presence of a base:

for the reaction of Ia with carbonyl halides and anhydrides to give amides and imides, respectively, see Henecka in Houben-Weyl, Methoden der Organischen Chemie, Volume 8, pages 653–713;

for the reaction of Ia with sulfonyl chlorides to give sulfonamides, see Mutz in Houben-Weyl, Methoden der Organischen Chemie, Volume 9, pages 599–658;

for the reaction of Ia with iso(thio)cyanates to give (thio)ureas, see Petersen in Houben-Weyl, Methoden der Organischen Chemie, Volume 8, pages 129–136;

for the reaction of Ia with aromatic aldehydes to give Schiff bases, see Freytag in Houben-Weyl, Volume 11/2, pages 73–98.

Examples of suitable solvents are aliphatic hydrocarbons, such as n-hexane, gasoline and petroleum ether, aromatic hydrocarbons, such as benzene, toluene and o-, m- and p-xylene, chlorohydrocarbons, such as dichloromethane, chloroform, tetrachloromethane, 1,2-dichloroethane and chlorobenzene, nitrogen-containing heteroaromatics, such as pyridine and quinoline, cyclic ethers, such as tetrahydrofuran and dioxane, nitriles, such as acetonitrile and propionitrile and dimethylformamide, dimethyl sulfoxide and N-methylpyrrolidone, or a mixture of the stated solvents. In the presence of phase transfer catalysts, the reaction can also be carried out in a 2-phase system of water and a hydrocarbon, eg. carbon tetrachloride.

Regarding the usable bases, phase transfer catalysts, the amounts and the pressure, the data given for method (a) are applicable.

In general, the reaction temperature is from 0° to 200° C., preferably from 20° to 140° C. in particular the boiling point of the relevant solvent.

The electrophilic compounds IV to IX are known or are obtainable by known processes (cf. Sustmann in Houben-Weyl: Methoden der Organischen Chemie, Volume E5, pages 590–608 and 634–652). The educts VIIa and VIIb are advantageously prepared in situ from halosulfonyl isocyanates and reactive compounds $R^1$—H, and the compounds VIIIa and VIIIb are prepared in a similar manner from isocyanate salts, such as ammonium isocyanate and compounds Hal—CY—$R^9$.

The substituted 5-aminopyrazoles I and I' are suitable as antidotes for making herbicidal active ingredients move compatible with crops such as millet, rice, corn, cereals (wheat, rye, barley and oats), cotton, sugar beet, sugar cane and soybean. They have an antagonistic effect on herbicides of a very wide range of classes, such as triazines, phenylurea derivatives, carbamates, thiocarbamates, haloacetanilides, benzoic acid derivatives and in particular halophenoxyacetic esters, substituted phenoxyphenoxyacetic esters, phenoxyphenoxypropionic esters and cyclohexenone derivatives.

Herbicidal active ingredients from the group consisting of the 2-(4-hetaryloxy)- or 2-(4-aryloxy)phenoxyacetic acid derivatives of the formula X

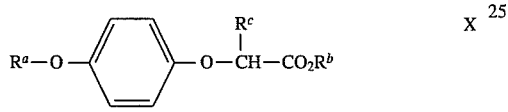

where $R^a$ is phenyl, pyridyl, benzoxazyl, benzothiazyl or benzopyrazinyl, where these aromatic ring systems may carry up to two of the following radicals: halogen, nitro, $C_1$–$C_4$-alkyl, $C_1$–$C_4$-haloalkyl and/or $C_1$–$C_4$-haloalkoxy, $R^b$ is hydrogen, $C_1$–$C_4$-alkyl or one equivalent of a plant-tolerated cation and $R^c$ is hydrogen or methyl, are disclosed in the literature, for example in DE-A-22 23 894, DE-A-24 33 067, DE-A-25 76 251, DE-A-30 04 770, BE-A-868 875 and BE-A-858 618.

They are used for controlling undesirable plants from the Gramineae family. However, the compatibility of these substances with crops varies from commercially acceptable to non-tolerated, depending on the substituents and application rate.

The same applies to cyclohexenone derivatives of the formula XI

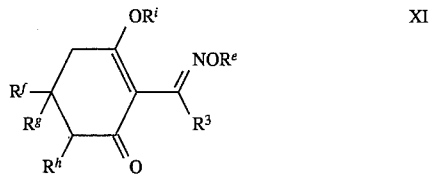

where $R^d$ is $C_1$–$C_4$-alkyl, such as methyl, ethyl, n-propyl, isopropyl, n-butyl or tert-butyl, preferably ethyl or n-propyl;

$R^e$ is $C_1$–$C_4$-alkyl, such as methyl, ethyl, n-propyl, isopropyl, n-butyl or tert-butyl, preferably ethyl or n-propyl, $C_a$- or $C_4$-alkenyl, preferably prop-2-enyl, $C_3$- or $C_4$-alkinyl or $C_3$- or $C_4$-haloalkenyl, preferably 3-chloroprop-2-en-1-yl, a $C_1$–$C_4$-alkylene or $C_2$–$C_4$-alkenylene chain, both of which may furthermore carry from one to three $C_1$–$C_3$-alkyl radicals and/or halogen atoms, or a 3-membered to 6-membered alkylene or 4-membered to 6-membered alkenylene chain which may be substituted by $C_1$–$C_3$-alkyl and each of which contains as a chain member an oxygen or sulfur atom not directly adjacent to the oxime ether moiety, all the abovementioned chains carrying as a terminal group the phenyl ring which in turn may be substituted by from one to three radicals selected from a group consisting of a benzyloxycarbonyl or phenyl radical and from one to three of each of the following radicals: nitro, cyano, halogen, $C_1$–$C_4$-alkyl, $C_1$–$C_4$-alkoxy, $C_1$–$C_4$-alkylthio, partially or completely halogenated $C_1$–$C_4$-alkyl, partially or completely halogenated $C_1$–$C_4$-alkoxy, carboxyl and $C_1$–$C_4$-alkoxycarbonyl, and it being possible for the phenyl ring furthermore to carry a number of halogen atoms such that the total number of radicals is 4 or 5; 4-(p-fluorophenyl)-but-3-enyl, 4-(p-chlorophenyl)-but-3-enyl and 2-(p-chlorophenoxy)-propyl are particularly preferred;

thienyl as stated for $R^d$, which may carry a halogen atom;

$R^5$ is $C_1$–$C_4$-alkyl which may be monosubstituted or disubstituted by $C_1$–$C_4$-alkylthio or by $C_1$–$C_4$-alkoxy, a 5-membered or 6-membered saturated or monounsaturated ring system which, in addition to carbon atoms, may carry an oxygen or sulfur atom or a sulfinyl or sulfonyl group, preferably tetrahydropyranyl, dihydropyranyl and tetrahydrothiopyranyl, where the ring system may furthermore carry from one to three radicals selected from the group consisting of hydroxyl, halogen, $C_1$–$C_4$-alkyl, $C_1$–$C_4$-haloalkyl, $C_1$–$C_4$-alkoxy and/or $C_1$–$C_4$-alkylthio, a 10-membered saturated or monounsaturated heterocyclic structure which contains two non-adjacent oxygen atoms or sulfur atoms and may be substituted by up to three $C_1$–$C_4$-alkyl groups and/or methoxy groups, phenyl, pyridyl, thiazolyl, pyrazolyl, pyrrolyl or isoxazolyl, where these groups may each carry from one to three, preferably one or two, radicals selected from the group consisting of: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkinyloxy, $C_1$–$C_4$-alkoxy-$C_1$–$C_3$-alkyl, $C_1$–$C_4$-dialkoxy-$C_1$–$C_3$-alkyl, formyl, halogen and benzoylamino;

$R^g$ is hydrogen or hydroxyl or, when $R^f$ is $C_1$–$C_6$-alkyl, is $C_1$–$C_6$-alkyl, preferably hydrogen;

$R^h$ is hydrogen, cyano, halogen, $C_1$–$C_4$-alkoxycarbonyl or a $C_1$–$C_4$-alkylketoxime group, preferably hydrogen; and $R^i$ is hydrogen or one equivalent of an agriculturally useful cation.

They are likewise described in the literature (for example EP-A 228 598, EP-A 230 235, EP-A 238 021, EP-A 368 227, U.S. Pat. No. 4,432,786, DE-A 24 39 104, DE-A 40 14 986 and DE-A 40 33 423) as herbicides and are used predominantly for controlling undesirable grasses in dicotyledon crops and in grasses which do not belong to the Gramineae family. Depending on the structure of the substituents and the dose used, compounds of this group can also be employed for selectively controlling undesirable grasses in gramineous crops, such as wheat and rice.

Cyclohexenone derivatives of the formula XI in which $R^e$ is an unsubstituted or substituted alkyl or alkenyl, eg. butyl or butenylphenyl, radical can be prepared in a conventional manner from known derivatives of the formula XII (EP-A 80 301, EP-A 125 094, EP-A 142 741, U.S. Pat. No. 4,249,937, EP-A 137 174 and EP-A 177 913) and the corresponding hydroxylamines of the formula XIII (Houben-Weyl, 10/1, page 1181 et seq.) (EP-A 169 521).

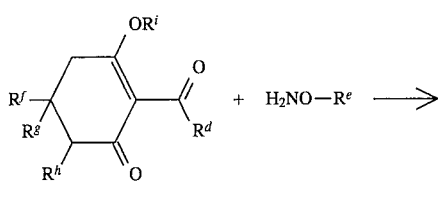

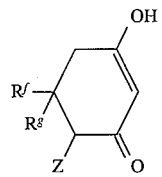

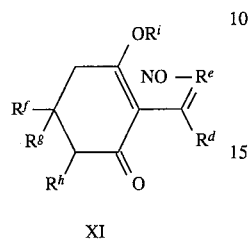

The reaction is advantageously carried out in the heterogeneous phase in a solvent at an adequate temperature below about 80° C., in the presence of a base, and the hydroxylamine XIII is used in the form of its ammonium salt.

Examples of suitable bases are carbonates, bicarbonates, acetates, alcoholates or oxides of alkali or alkaline earth metals, in particular sodium hydroxide, potassium hydroxide, magnesium oxide and calcium oxide. Organic bases, such as pyridine or tertiary amines, can also be used. The base is added, for example, in an amount of from 0.5 to 2 mol equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol using sodium bicarbonate as the base.

The reaction is complete after a few hours. The target compound can be isolated, for example, by evaporating down the mixture, partitioning the residue between methylene chloride and water and distilling off the solvent under reduced pressure.

However, it is also possible directly to use the free hydroxylamine base, for example in the form of an aqueous solution, for this reaction; a single-phase or two-phase reaction mixture is obtained, depending on the solvent used for the compound XII.

Examples of suitable solvents for this version are alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds XI can be obtained by treating the 3-hydroxy compounds with sodium hydroxide, potassium hydroxide or sodium or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts by means of ammonia or ammonium, phosphonium, sulfonium or sulfoxonium hydroxides.

The compounds of type XII can be prepared, for example, from the corresponding cyclohexane-1,3-diones of the formula XIV

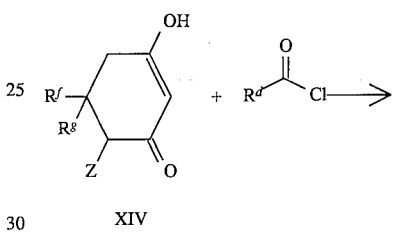

where Z is hydrogen or methoxycarbonyl and $R^g$ is hydrogen, by known methods (Tetrahedron Lett. (1975), 2491).

It is also possible to prepare the compounds of the formula XII via the enol ester intermediates, which are obtained in the reaction of compounds of the formula XIV with acid chlorides in the presence of a base and are then subjected to a rearrangement reaction with certain imidazole or pyridine derivatives (Japanese Preliminary Published Application 79/063 052).

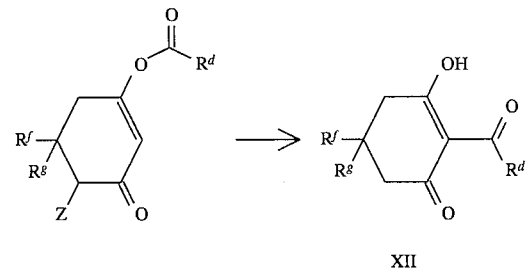

The compounds of the formula XIV are obtained by a number of known process steps, starting from known precursors.

The hydroxylamines XIII in which $R^e$ is unsubstituted or substituted phenylbutyl are synthesized according to the following reaction scheme, for example by a) alkylation of cyclic hydroxyimides XV with suitable phenylbutyl halides and subsequent elimination of the protective group, for example with hydrazine or ethanolamine, similarly to Examples from EP-A 244 786 or Houben-Weyl, Methoden der organischen Chemie, Volume X/1, page 1152 et seq. or b) hydrogenation of N-4-phenylbutenyloxyphthalimides whose preparation is described in DE-A 38 38 310, by means of suitable catalysts, for example palladium on active carbon, in suitable inert solvents, such as methanol, tetrahydrofuran or dioxane, and subsequent elimination of the protective group as described above.

The hydrogenation is advantageously carried out at from 20° C. to the boiling point of the solvent, in particular at room temperature, by a conventional method, at atmospheric, superatmospheric or reduced pressure. A pressure of from 1 to 10, in particular 1 to 2, bar is preferred.

Reaction scheme:

Route a)

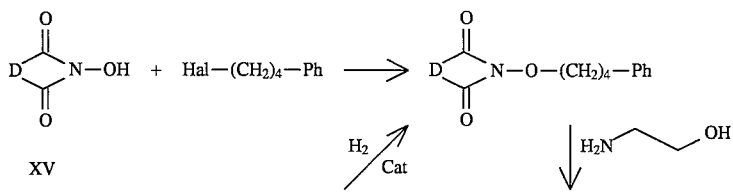

Route b)

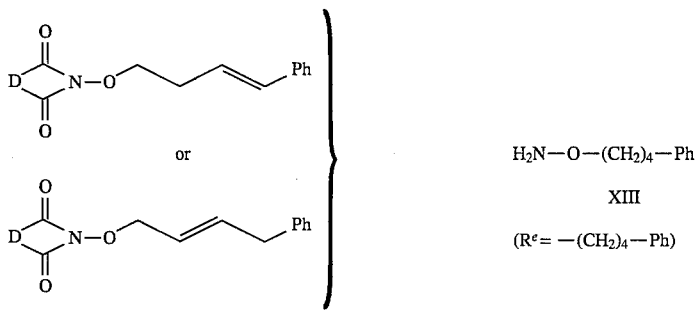

Ph=unsubstituted or substituted phenyl

Examples of suitable cyclic hydroxyimides XV are the following substances:

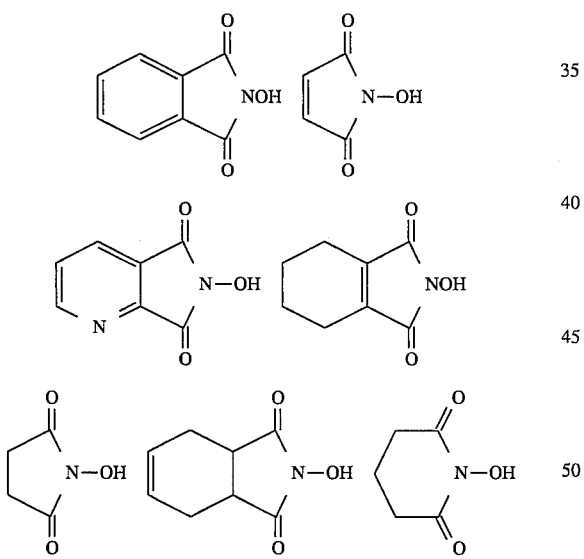

The hydroxylamines XIII in which $R^e$ is unsubstituted or substituted butenylphenyl and the phenyl radical abbreviated below to Ph may in turn be substituted or unsubstituted are synthesized according to the following reaction scheme by diazotization of aniline derivatives and subsequent coupling of the diazonium salt to a correspondingly substituted butadiene XVI. The resulting mixture of XVIIa and XVIIb is coupled to a cyclic hydroxyimide XV, and the protected hydroxylamine derivative XVIII obtained is cleaved with 2-aminoethanol to give the free hydroxylamine XIII:

Route c)

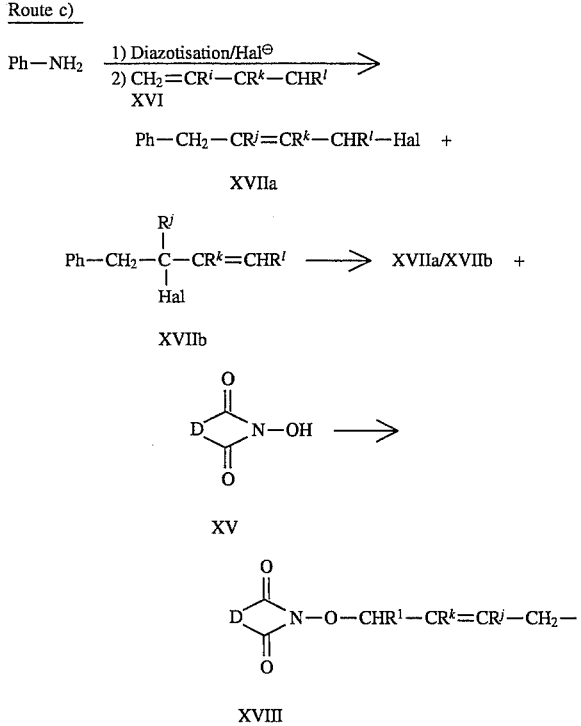

The radicals $R^j$, $R^k$ and $R^l$ independently of one another are each hydrogen, $C_1$-$C_3$-alkyl and/or halogen. Hal is halogen, preferably chlorine or bromine.

The halides XVIIa required for the above synthesis of the hydroxylamines of the formula XIII can be prepared as a mixture with XVIIb by processes known from the literature, for example by reacting diazonium salts of aromatic or heteroaromatic anilines with dienes. The range of application of the reaction is discussed in Organic Reactions 11 (1960), 189 or 24 (1976), 225.

Coupling of the isomeric halides XVIa and XVIb to a cyclic hydroxyimide of the formula XV gives exclusively the cyclic imido ethers of the formula XVIII, which, after elimination of the protective group on the nitrogen, give the hydroxylamines XIII.

The reaction with a hydroxyimide XIV (Routes a and c) is carried out in the presence of an acid acceptor and of a solvent. For cost reasons, hydroxyphthalimide is preferably used as the hydroxyimide XV.

Suitable acid acceptors are alkali metal carbonates, such as potassium carbonate or sodium carbonate, alkali metal bicarbonates, such as potassium bicarbonate or sodium bicarbonate, tertiary amines, such as trimethylamine or triethylamine, and basic heterocycles, such as pyridine. For cost reasons, potassium carbonate and sodium carbonate are preferred.

Suitable solvents are aprotic dipolar organic solvents, eg. dimethylformamide, dimethyl sulfoxide and/or sulfolane.

Alkylation under phase transfer conditions is also possible. The organic solvents used here are water-immiscible compounds, such as hydrocarbons or chlorohydrocarbons. Suitable phase transfer catalysts are quaternary ammonium and phosphonium salts.

The cleavage of the cyclic imido ethers XVIII is carried out similarly to a process described in EP-A 244 786, using alkanolamines. The hydroxylamines XIII can be isolated by this process as free bases or as salts after precipitation with acids. Readily crystallizing salts are obtained by reacting the bases with oxalic acid.

Specific examples of herbicidal (hetaryloxy)- or aryloxyphenoxyacetic acid derivatives of the formula X whose toleration by crops can be improved by substituted 5-aminopyrazoles I or I' are shown in Table 1 below.

TABLE 1

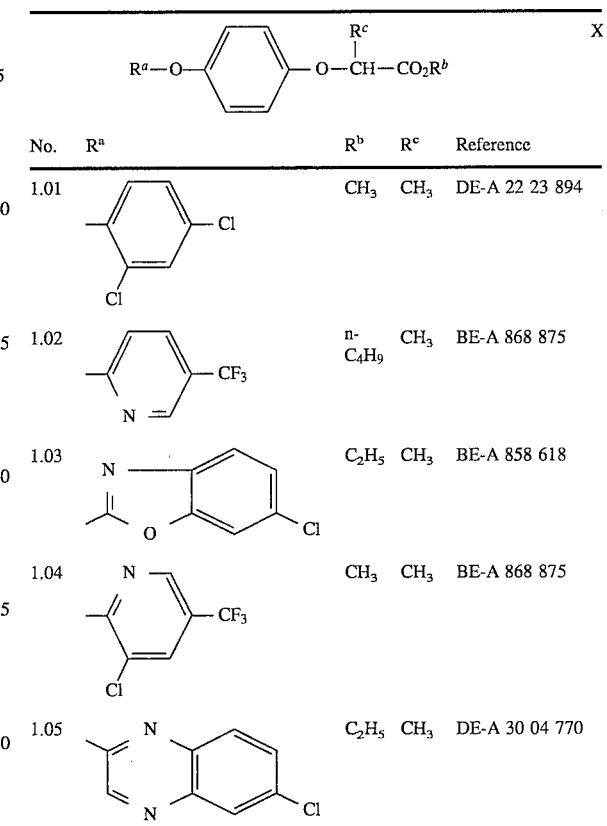

Specific examples of herbicidal cyclohexenones of the formula XI whose toleration by crops can be improved by substituted 5-aminopyrazoles I or I' are shown in Tables 2 to 13 below.

TABLE 2

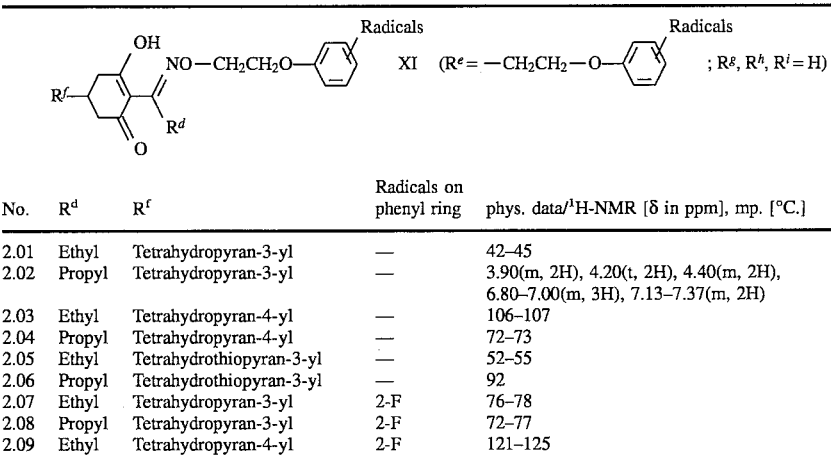

| No. | $R^d$ | $R^f$ | Radicals on phenyl ring | phys. data/$^1$H-NMR [$\delta$ in ppm], mp. [°C.] |
|---|---|---|---|---|
| 2.01 | Ethyl | Tetrahydropyran-3-yl | — | 42–45 |
| 2.02 | Propyl | Tetrahydropyran-3-yl | — | 3.90(m, 2H), 4.20(t, 2H), 4.40(m, 2H), 6.80–7.00(m, 3H), 7.13–7.37(m, 2H) |
| 2.03 | Ethyl | Tetrahydropyran-4-yl | — | 106–107 |
| 2.04 | Propyl | Tetrahydropyran-4-yl | — | 72–73 |
| 2.05 | Ethyl | Tetrahydrothiopyran-3-yl | — | 52–55 |
| 2.06 | Propyl | Tetrahydrothiopyran-3-yl | — | 92 |
| 2.07 | Ethyl | Tetrahydropyran-3-yl | 2-F | 76–78 |
| 2.08 | Propyl | Tetrahydropyran-3-yl | 2-F | 72–77 |
| 2.09 | Ethyl | Tetrahydropyran-4-yl | 2-F | 121–125 |

TABLE 2-continued

XI ($R^e$ = —CH$_2$CH$_2$—O—〈phenyl〉 ; $R^g$, $R^h$, $R^i$ = H)

| No. | $R^d$ | $R^f$ | Radicals on phenyl ring | phys. data/$^1$H-NMR [δ in ppm], mp. [°C.] |
|---|---|---|---|---|
| 2.10 | Propyl | Tetrahydropyran-4-yl | 2-F | 103–107 |
| 2.11 | Ethyl | Tetrahydrothiopyran-3-yl | 2-F | 82–86 |
| 2.12 | Propyl | Tetrahydrothiopyran-3-yl | 2-F | 81–85 |
| 2.13 | Ethyl | Tetrahydropyran-3-yl | 3-F | 62–68 |
| 2.14 | Propyl | Tetrahydropyran-3-yl | 3-F | 3.90(m, 2H), 4.20(t, 2H), 4.40(m, 2H) 6.70(m, 3H), 7.25(m, 1H), |
| 2.15 | Ethyl | Tetrahydropyran-4-yl | 3-F | 103–109 |
| 2.16 | Propyl | Tetrahydropyran-4-yl | 3-F | 73–79 |
| 2.17 | Ethyl | Tetrahydrothiopyran-3-yl | 3-F | 4.20(t, 2H), 4.40(m, 2H) 6.70(m, 3H), 7.25(m, 1H) |
| 2.18 | Propyl | Tetrahydrothiopyran-3-yl | 3-F | |
| 2.19 | Ethyl | Tetrahydropyran-3-yl | 4-F | 64–67 |
| 2.20 | Propyl | Tetrahydropyran-3-yl | 4-F | 70–72 |
| 2.21 | Ethyl | Tetrahydropyran-4-yl | 4-F | 101–103 |
| 2.22 | Propyl | Tetrahydropyran-4-yl | 4-F | 107–109 |
| 2.23 | Ethyl | Tetrahydrothiopyran-3-yl | 4-F | 105–108 |
| 2.24 | Propyl | Tetrahydrothiopyran-3-yl | 4-F | 82–84 |
| 2.25 | Ethyl | Tetrahydropyran-3-yl | 2-Cl | 74–80 |
| 2.26 | Propyl | Tetrahydropyran-3-yl | 2-Cl | 67–71 |
| 2.27 | Ethyl | Tetrahydropyran-4-yl | 2-Cl | 4.00(m, 2H), 4.27(t, 2H), 4.47(m, 2H), 7.20(t, 1H), 7.37(d, 1H) |
| 2.28 | Propyl | Tetrahydropyran-4-yl | 2-Cl | 68–72 |
| 2.29 | Ethyl | Tetrahydrothiopyran-3-yl | 2-Cl | 74–78 |
| 2.30 | Propyl | Tetrahydrothiopyran-3-yl | 2-Cl | 72–78 |
| 2.31 | Ethyl | Tetrahydropyran-3-yl | 3-Cl | |
| 2.32 | Propyl | Tetrahydropyran-3-yl | 3-Cl | |
| 2.33 | Ethyl | Tetrahydropyran-4-yl | 3-Cl | |
| 2.34 | Propyl | Tetrahydropyran-4-yl | 3-Cl | |
| 2.35 | Ethyl | Tetrahydrothiopyran-3-yl | 3-Cl | |
| 2.36 | Propyl | Tetrahydrothiopyran-3-yl | 3-Cl | |
| 2.37 | Ethyl | Tetrahydropyran-3-yl | 4-Cl | 3.93(m, 2H), 4.20(t, 2H), 4.43(m, 2H), 6.90(m, 2H), 7.25(m, 2H) |
| 2.38 | Propyl | Tetrahydropyran-3-yl | 4-Cl | 3.93(m, 2H), 4.20(t, 2H), 4.43(m, 2H), 6.90(m, 2H), 7.25(m, 2H) |
| 2.39 | Ethyl | Tetrahydropyran-4-yl | 4-Cl | 116–118 |
| 2.40 | Propyl | Tetrahydropyran-4-yl | 4-Cl | 104–106 |
| 2.41 | Ethyl | Tetrahydrothiopyran-3-yl | 4-Cl | 74–77 |
| 2.42 | Propyl | Tetrahydrothiopyran-3-yl | 4-Cl | 86–88 |
| 2.43 | Ethyl | Tetrahydropyran-3-yl | 2-CF$_3$ | |
| 2.44 | Propyl | Tetrahydropyran-3-yl | 2-CF$_3$ | |
| 2.45 | Ethyl | Tetrahydropyran-4-yl | 2-CF$_3$ | |
| 2.46 | Propyl | Tetrahydropyran-4-yl | 2-CF$_3$ | |
| 2.47 | Ethyl | Tetrahydrothiopyran-3-yl | 2-CF$_3$ | |
| 2.48 | Propyl | Tetrahydrothiopyran-3-yl | 2-CF$_3$ | |
| 2.49 | Ethyl | Tetrahydropyran-3-yl | 3-CF$_3$ | |
| 2.50 | Propyl | Tetrahydropyran-3-yl | 3-CF$_3$ | |
| 2.51 | Ethyl | Tetrahydropyran-4-yl | 3-CF$_3$ | |
| 2.52 | Propyl | Tetrahydropyran-4-yl | 3-CF$_3$ | |
| 2.53 | Ethyl | Tetrahydrothiopyran-3-yl | 3-CF$_3$ | |
| 2.54 | Propyl | Tetrahydrothiopyran-3-yl | 3-CF$_3$ | |
| 2.55 | Ethyl | Tetrahydropyran-3-yl | 4-CF$_3$ | 72–77 |
| 2.56 | Propyl | Tetrahydropyran-3-yl | 4-CF$_3$ | 3.90(m, 2H), 4.27(t, 2H), 4.47(m, 2H) 7.00(d, 2H), 7.55(d, 2H) |
| 2.57 | Ethyl | Tetrahydropyran-4-yl | 4-CF$_3$ | |
| 2.58 | Propyl | Tetrahydropyran-4-yl | 4-CF$_3$ | 90–94 |
| 2.59 | Ethyl | Tetrahydrothiopyran-3-yl | 4-CF$_3$ | 73–79 |
| 2.60 | Propyl | Tetrahydrothiopyran-3-yl | 4-CF$_3$ | 4.27(t, 2H), 4.47(m, 2H), 7.00(d, 2H) 7.55(d, 2H) |
| 2.61 | Ethyl | Tetrahydropyran-3-yl | 2,4-Cl$_2$ | 73–75 |
| 2.62 | Propyl | Tetrahydropyran-3-yl | 2,4-Cl$_2$ | 69–73 |
| 2.63 | Ethyl | Tetrahydropyran-4-yl | 2,4-Cl$_2$ | 4.00(m, 2H), 4.25(t, 2H), 4.45(t, 2H) 6.87(d, 1H), 7.17(d, 1H), 7.37(d, 1H) |
| 2.64 | Propyl | Tetrahydropyran-4-yl | 2,4-Cl$_2$ | 4.00(m, 2H), 4.25(t, 2H), 4.45(t, 2H) 6.87(d, 1H), 7.17(d, 1H), 7.37(d, 1H) |
| 2.65 | Ethyl | Tetrahydrothiopyran-3-yl | 2,4-Cl$_2$ | 4.25(t, 2H), 4.45(t, 2H), 6.87(d, 1H) 7.17(d, 1H), 7.37(d, 1H) |
| 2.66 | Propyl | Tetrahydrothiopyran-3-yl | 2,4-Cl$_2$ | 4.25(t, 2H), 4.45(t, 2H), 6.87(d, 1H) 7.17(d, 1H), 7.37(d, 1H) |

TABLE 2-continued

XI ($R^e = -CH_2CH_2-O-\phenyl$ ; $R^g, R^h, R^i = H$)

| No. | $R^d$ | $R^f$ | Radicals on phenyl ring | phys. data/$^1$H-NMR [δ in ppm], mp. [°C.] |
|---|---|---|---|---|
| 2.67 | Ethyl | Tetrahydropyran-3-yl | 2,4,6-Cl$_3$ | 90–93 |
| 2.68 | Propyl | Tetrahydropyran-3-yl | 2,4,6-Cl$_3$ | 83–87 |
| 2.69 | Ethyl | Tetrahydropyran-4-yl | 2,4,6-Cl$_3$ | 79–82 |
| 2.70 | Propyl | Tetrahydropyran-4-yl | 2,4,6-Cl$_3$ | 4.00(m, 2H), 4.27(t, 2H), 4.45(m, 2H), 7.32(s, 2H) |
| 2.71 | Ethyl | Tetrahydrothiopyran-3-yl | 2,4,6-Cl$_3$ | 105–108 |
| 2.72 | Propyl | Tetrahydrothiopyran-3-yl | 2,4,6-Cl$_3$ | 4.27(t, 2H), 4.45(m, 2H), 7.82(s, 2H) |
| 2.73 | Ethyl | Tetrahydropyran-3-yl | 4-NO$_2$ | 3.90(m, 2H), 4.32(m, 2H), 4.50(m, 2H), 7.00(d, 2H), 8.20(d, 2H) |
| 2.74 | Propyl | Tetrahydropyran-3-yl | 4-NO$_2$ | 3.90(m, 2H), 4.32(m, 2H), 4.50(m, 2H) 7.00(d, 2H), 8.20(d, 2H) |
| 2.75 | Ethyl | Tetrahydropyran-4-yl | 4-NO$_2$ | 126–129 |
| 2.76 | Propyl | Tetrahydropyran-4-yl | 4-NO$_2$ | 138–141 |
| 2.77 | Ethyl | Tetrahydrothiopyran-3-yl | 4-NO$_2$ | 4.32(m, 2H), 4.50(m, 2H), 7.00(d, 2H), 8.20(d, 2H) |
| 2.78 | Propyl | Tetrahydrothiopyran-3-yl | 4-NO$_2$ | 4.32(m, 2H), 4.50(m, 2H), 7.00(d, 2H) 8.20(d, 2H) |

TABLE 3

XI ($R^e = -CH_2CH(CH_3)-O-\phenyl$ ; $R^g, R^h, R^i = H$)

| No. | $R^d$ | $R^f$ | Radicals on phenyl ring | phys. data/$^1$H-NMR [δ in ppm], mp. [°C.] |
|---|---|---|---|---|
| 3.01 | Ethyl | Tetrahydropyran-3-yl | — | |
| 3.02 | Propyl | Tetrahydropyran-3-yl | — | |
| 3.03 | Ethyl | Tetrahydropyran-4-yl | — | |
| 3.04 | Propyl | Tetrahydropyran-4-yl | — | |
| 3.05 | Ethyl | Tetrahydrothiopyran-3-yl | — | |
| 3.06 | Propyl | Tetrahydrothiopyran-3-yl | — | |
| 3.07 | Ethyl | Tetrahydropyran-3-yl | 4-F | |
| 3.08 | Propyl | Tetrahydropyran-3-yl | 4-F | |
| 3.09 | Ethyl | Tetrahydropyran-4-yl | 4-F | |
| 3.10 | Propyl | Tetrahydropyran-4-yl | 4-F | |
| 3.11 | Ethyl | Tetrahydrothiopyran-3-yl | 4-F | |
| 3.12 | Propyl | Tetrahydrothiopyran-3-yl | 4-F | |
| 3.13 | Ethyl | Tetrahydropyran-3-yl | 4-Cl | |
| 3.14 | Propyl | Tetrahydropyran-3-yl | 4-Cl | |
| 3.15 | Ethyl | Tetrahydropyran-4-yl | 4 Cl | 1.35(m, 3H), 4.05–4.30(m, 2H), 4.60(m, 1H), 6.80–7.40(m, 4H) |
| 3.16 | Propyl | Tetrahydropyran-4-yl | 4-Cl | 1.35(m, 3H), 4.05–4.30(m, 2H), 4.60(m, 1H), 6.80–7.40(m, 4H) |
| 3.17 | Ethyl | Tetrahydrothiopyran-3-yl | 4-Cl | 1.35(m, 3H), 4.05–4.25(m, 2H), 4.60(m, 1H), 6.80–7.40(m, 4H) |
| 3.18 | Propyl | Tetrahydrothiopyran-3-yl | 4-Cl | 1.35(m, 3H), 4.05–4.30(m, 2H), 4.60(m, 1H), 6.80–7.40(m, 4H) |

TABLE 4

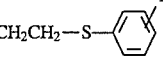

| No. | $R^d$ | $R^f$ | Radicals on phenyl ring | phys. data/$^1$H-NMR [$\delta$ in ppm], mp. [°C.] |
|---|---|---|---|---|
| 4.01 | Ethyl | Tetrahydropyran-3-yl | — | 3.90(m, 2H), 4.23(t, 2H), 7.17–7.43(m, 5H) |
| 4.02 | Propyl | Tetrahydropyran-3-yl | — | 65 |
| 4.03 | Ethyl | Tetrahydropyran-4-yl | — | 3.97(m, 2H), 4.23(t, 2H), 7.17–7.43(m, 5H) |
| 4.04 | Propyl | Tetrahydropyran-4-yl | — | 3.97(m, 2H), 4.23(t, 2H), 7.17–7.43(m, 5H) |
| 4.05 | Ethyl | Tetrahydrothiopyran-3-yl | — | 4.23(t, 2H), 7.17–7.43(m, 5H) |
| 4.06 | Propyl | Tetrahydrothiopyran-3-yl | — | 4.23(t, 2H), 7.17–7.43(m, 5H) |
| 4.07 | Ethyl | Tetrahydropyran-3-yl | 4-F | 3.90(m, 2H), 4.17(t, 2H), 7.00(m, 2H), 7.40(m, 2H) |
| 4.08 | Propyl | Tetrahydropyran-3-yl | 4-F | 3.90(m, 2H), 4.17(t, 2H), 7.00(m, 2H), 7.40(m, 2H) |
| 4.09 | Ethyl | Tetrahydropyran-4-yl | 4-F | 4.00(m, 2H), 4.17(t, 2H), 7.00(m, 2H), 7.40(m, 2H) |
| 4.10 | Propyl | Tetrahydropyran-4-yl | 4-F | 4.00(m, 2H), 4.17(t, 2H), 7.00(m, 2H), 7.40(m, 2H) |
| 4.11 | Ethyl | Tetrahydrothiopyran-3-yl | 4-F | 4.17(t, 2H), 7.00(m, 2H), 7.40(m, 2H), |
| 4.12 | Propyl | Tetrahydrothiopyran-3-yl | 4-F | 4.17(t, 2H), 7.00(m, 2H), 7.40(m, 2H), |
| 4.13 | Ethyl | Tetrahydropyran-3-yl | 4-Cl | 71–75 |
| 4.14 | Propyl | Tetrahydropyran-3-yl | 4-Cl | 63–65 |
| 4.15 | Ethyl | Tetrahydropyran-4-yl | 4-Cl | 4.00(m, 2H), 4.20(t, 2H), 7.30(m, 4H) |
| 4.16 | Propyl | Tetrahydropyran-4-yl | 4-Cl | 4.00(m, 2H), 4.20(t, 2H), 7.30(m, 4H) |
| 4.17 | Ethyl | Tetrahydrothiopyran-3-yl | 4-Cl | 4.20(t, 2H), 7.30(m, 4H) |
| 4.18 | Propyl | Tetrahydrothiopyran-3-yl | 4-Cl | 4.20(t, 2H), 7.30(m, 4H) |
| 4.19 | Ethyl | Tetrahydropyran-3-yl | 2-Cl | 3.90(m, 2H), 4.25(t, 2H), 7.10–7.50(m, 4H) |
| 4.20 | Propyl | Tetrahydropyran-3-yl | 2-Cl | 3.90(m, 2H), 4.25(t, 2H), 7.10–7.50(m, 4H) |
| 4.21 | Ethyl | Tetrahydropyran-4-yl | 2-Cl | 4.00(m, 2H), 4.25(t, 2H), 7.10–7.50(m, 4H) |
| 4.22 | Propyl | Tetrahydropyran-4-yl | 2-Cl | 4.00(m, 2H), 4.25(t, 2H), 7.10–7.50(m, 4H) |
| 4.23 | Ethyl | Tetrahydrothiopyran-3-yl | 2-Cl | 4.25(t, 2H) 7.10–7.50(m, 4H) |
| 4.24 | Propyl | Tetrahydrothiopyran-3-yl | 2-Cl | 4.25(t, 2H) 7.10–7.50(m, 4H) |
| 4.25 | Ethyl | Tetrahydropyran-3-yl | 2,6-Cl$_2$ | 3.90(m, 2H) 4.20(t, 2H), 7.20(t, 1H) 7.40(d, 2H) |
| 4.26 | Propyl | Tetrahydropyran-3-yl | 2,6-Cl$_2$ | 3.90(m, 2H) 4.20(t, 2H), 7.20(t, 1H) 7.40(d, 2H) |
| 4.27 | Ethyl | Tetrahydropyran-4-yl | 2,6-Cl$_2$ | 61–64 |
| 4.28 | Propyl | Tetrahydropyran-4-yl | 2,6-Cl$_2$ | 4.00(m, 2H) 4.20(t, 2H), 7.20(t, 1H) 7.40(d, 2H) |
| 4.29 | Ethyl | Tetrahydrothiopyran-3-yl | 2,6-Cl$_2$ | 4.20(t, 2H) 7.20(t, 2H), 7.40(d, 2H) |
| 4.30 | Propyl | Tetrahydrothiopyran-3-yl | 2,6-Cl$_2$ | 4.20(t, 2H) 7.20(t, 2H), 7.40(d, 2H) |

TABLE 5

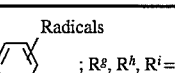

| No. | $R^d$ | $R^f$ | Radicals on phenyl ring | phys. data/$^1$H-NMR [$\delta$ in ppm], mp. [°C.] |
|---|---|---|---|---|
| 5.01 | Ethyl | Tetrahydropyran-3-yl | — | 3.90(m, 2H), 4.03(t, 2H), 4.23(t, 2H), 6.90(m, 3H), 7.27(m, 2H) |
| 5.02 | Propyl | Tetrahydropyran-3-yl | — | 3.90(m, 2H), 4.03(t, 2H), 4.23(t, 2H), 6.90(m, 3H), 7.27(m, 2H) |
| 5.03 | Ethyl | Tetrahydropyran-4-yl | — | 3.97(m, 2H), 4.03(t, 2H), 4.23(t, 2H), 6.90(m, 3H), 7.27(m, 2H) |
| 5.04 | Propyl | Tetrahydropyran-4-yl | — | 3.97(m, 2H), 4.03(t, 2H), 4.23(t, 2H), 6.90(m, 3H), 7.27(m, 2H) |
| 5.05 | Ethyl | Tetrahydrothiopyran-3- | — | 4.03(t, 2H), 4.23(t, 2H), 6.90(m, 3H), 7.27(m, 2H) |
| 5.06 | Propyl | Tetrahydrothiopyran-3- | — | 4.03(t, 2H), 4.23(t, 2H), 6.90(m, 3H), 7.27(m, 2H) |

TABLE 5-continued $$\text{Structure: cyclohexenone with OH, } R^f, R^d, \text{ and } =N-O-CH_2CH_2CH_2-O-\text{phenyl(Radicals)}$$

XI ($R^e = -CH_2CH_2-CH_2-O-$phenyl(Radicals) ; $R^g, R^h, R^i = H$)

| No. | $R^d$ | $R^f$ | Radicals on phenyl ring | phys. data/$^1$H-NMR [δ in ppm], mp. [°C.] |
|---|---|---|---|---|
| 5.07 | Ethyl | Tetrahydropyran-3-yl | 2-F | 3.90(m, 2H), 4.10(t, 2H), 4.27(t, 2H), 6.80–7.15(m, 4H) |
| 5.08 | Propyl | Tetrahydropyran-3-yl | 2-F | 3.90(m, 2H), 4.10(t, 2H), 4.27(t, 2H), 6.80–7.15(m, 4H) |
| 5.09 | Ethyl | Tetrahydropyran-4-yl | 2-F | 4.00(m, 2H), 4.10(t, 2H), 4.27(t, 2H), 6.80–7.15(m, 4H) |
| 5.10 | Propyl | Tetrahydropyran-4-yl | 2-F | 76–80 |
| 5.11 | Ethyl | Tetrahydrothiopyran-3-yl | 2-F | 4.10(t, 2H), 4.27(t, 2H), 6.80–7.15(m, 4H), |
| 5.12 | Propyl | Tetrahydrothiopyran-3-yl | 2-F | 4.10(t, 2H), 4.27(t, 2H), 6.80–7.15(m, 4H), |
| 5.13 | Ethyl | Tetrahydropyran-3-yl | 3-F | 3.90(m, 2H), 4.05(t, 2H), 4.27(t, 2H), 6.67(m, 3H), 7.23(m, 1H) |
| 5.14 | Propyl | Tetrahydropyran-3-yl | 3-F | 3.90(m, 2H), 4.05(t, 2H), 4.27(t, 2H), 6.67(m, 3H), 7.23(m, 1H) |
| 5.15 | Ethyl | Tetrahydropyran-4-yl | 3-F | 3.90–4.10(m, 4H), 4.27(t, 2H), 6.67(m, 3H), 7.23(m, 1H) |
| 5.16 | Propyl | Tetrahydropyran-4-yl | 3-F | 3.90–4.10(m, 4H), 4.27(t, 2H), 6.67(m, 3H), 7.23(m, 1H) |
| 5.17 | Ethyl | Tetrahydrothiopyran-3-yl | 3-F | 4.05(t, 2H), 4.27(t, 2H), 6.67(m, 3H) 7.23(m, 1H) |
| 5.18 | Propyl | Tetrahydrothiopyran-3-yl | 3-F | 4.05(t, 2H), 4.27(t, 2H), 6.67(m, 3H) 7.23(m, 1H) |
| 5.19 | Ethyl | Tetrahydropyran-3-yl | 4-F | 3.90(m, 2H), 4.03(t, 2H), 4.27(t, 2H), 6.90(m, 2H), 7.00(m, 2H) |
| 5.20 | Propyl | Tetrahydropyran-3-yl | 4-F | 3.90(m, 2H), 4.03(t, 2H), 4.27(t, 2H), 6.90(m, 2H), 7.00(m, 2H) |
| 5.21 | Ethyl | Tetrahydropyran-4-yl | 4-F | 3.90–4.06(m, 4H), 4.23(t, 2H), 6.90(m, 2H), 7.00(m, 2H) |
| 5.22 | Propyl | Tetrahydropyran-4-yl | 4-F | 3.90–4.06(m, 4H), 4.28(t, 2H), 6.90(m, 2H), 7.00(m, 2H) |
| 5.23 | Ethyl | Tetrahydrothiopyran-3-yl | 4-F | 4.03(t, 2H), 4.27(t, 2H), 6.90(m, 2H), 7.00(m, 2H) |
| 5.24 | Propyl | Tetrahydrothiopyran-3-yl | 4-F | 4.03(t, 2H), 4.27(t, 2H), 6.90(m, 2H), 7.00(m, 2H) |
| 5.25 | Ethyl | Tetrahydropyran-3-yl | 2-Cl | |
| 5.26 | Propyl | Tetrahydropyran-3-yl | 2-Cl | |
| 5.27 | Ethyl | Tetrahydropyran-4-yl | 2-Cl | |
| 5.28 | Propyl | Tetrahydropyran-4-yl | 2-Cl | |
| 5.29 | Ethyl | Tetrahydrothiopyran-3-yl | 2-Cl | |
| 5.30 | Propyl | Tetrahydrothiopyran-3-yl | 2-Cl | |
| 5.31 | Ethyl | Tetrahydropyran-3-yl | 3-Cl | 3.90(m, 2H), 4.06(t, 2H), 4.27(t, 2H), 6.77(m, 1H), 6.90(m, 2H), 7.17(m, 1H) |
| 5.32 | Propyl | Tetrahydropyran-3-yl | 3-Cl | 3.90(m, 2H), 4.06(t, 2H), 4.27(t, 2H), 6.77(m, 1H), 6.90(m, 2H), 7.17(m, 1H) |
| 5.33 | Ethyl | Tetrahydropyran-4-yl | 3-Cl | 3.90–4.10(m, 4H), 4.27(t, 2H), 6.77(m, 1H), 6.90(m, 2H), 7.17(m, 1H) |
| 5.34 | Propyl | Tetrahydropyran-4-yl | 3-Cl | 3.90–4.10(m, 4H), 4.27(t, 2H), 6.77(m, 1H), 6.90(m, 2H), 7.17(m, 1H) |
| 5.35 | Ethyl | Tetrahydrothiopyran-3-yl | 3-Cl | 4.06(t, 2H), 4.27(t, 2H), 6.77(m, 1H), 6.90(m, 2H), 7.17(m, 1H) |
| 5.36 | Propyl | Tetrahydrothiopyran-3-yl | 3-Cl | 4.06(t, 2H), 4.27(t, 2H), 6.77(m, 1H), 6.90(m, 2H), 7.17(m, 1H) |
| 5.37 | Ethyl | Tetrahydropyran-3-yl | 4-Cl | 3.90(m, 2H), 4.03(t, 2H), 4.23(t, 2H), 6.80(m, 2H), 7.20(m, 2H) |
| 5.38 | Propyl | Tetrahydropyran-3-yl | 4-Cl | 3.90(m, 2H), 4.03(t, 2H), 4.23(t, 2H), 6.80(m, 2H), 7.20(m, 2H) |
| 5.39 | Ethyl | Tetrahydropyran-4-yl | 4-Cl | 3.90–4.09(m, 4H), 4.23(t, 2H), 6.80(m, 2H), 7.20(m, 2H) |
| 5.40 | Propyl | Tetrahydropyran-4-yl | 4-Cl | 3.90–4.09(m, 4H), 4.23(t, 2H), 6.80(m, 2H), 7.20(m, 2H) |
| 5.41 | Ethyl | Tetrahydrothiopyran-3-yl | 4-Cl | 4.03(t, 2H), 4.23(t, 2H), 6.80(m, 2H), 7.20(m, 2H) |
| 5.42 | Propyl | Tetrahydrothiopyran-3-yl | 4-Cl | 4.03(t, 2H), 4.23(t, 2H), 6.80(m, 2H), 7.20(m, 2H) |
| 5.43 | Ethyl | Tetrahydropyran-3-yl | 4-NO$_2$ | 3.90(m, 2H), 4.20(t, 2H), 4.28(t, 2H), 6.93(d, 2H), 8.20(d, H) |
| 5.44 | Propyl | Tetrahydropyran-3-yl | 4-NO$_2$ | 3.90(m, 2H), 4.20(t, 2H), 4.28(t, 2H), 6.93(d, 2H), 8.20(d, 2H) |
| 5.45 | Ethyl | Tetrahydropyran-4-yl | 4-NO$_2$ | 4.00(m, 2H), 4.20(t, 2H), 4.28(t, 2H), |

TABLE 5-continued

XI ($R^e = -CH_2CH_2-CH_2-O-\phi$ ; $R^g$, $R^h$, $R^i = H$)

| No. | $R^d$ | $R^f$ | Radicals on phenyl ring | phys. data/$^1$H-NMR [δ in ppm], mp. [°C.] |
|---|---|---|---|---|
| 5.46 | Propyl | Tetrahydropyran-4-yl | 4-NO$_2$ | 6.93(d, 2H), 8.20(d, 2H)<br>4.00(m, 2H), 4.20(t, 2H), 4.28(t, 2H),<br>6.93(d, 2H), 8.20(d, 2H) |
| 5.47 | Ethyl | Tetrahydrothiopyran-3-yl | 4-NO$_2$ | 4.20(t, 2H), 4.28(t, 2H), 6.93(d, 2H),<br>8.20(d, 2H) |
| 5.48 | Propyl | Tetrahydrothiopyran-3-yl | 4-NO$_2$ | 4.20(t, 2H), 4.28(t, 2H), 6.93(d, 2H),<br>8.20(d, 2H) |
| 5.49 | Ethyl | Tetrahydropyran-3-yl | 4-Br | 3.90(m, 2H), 4.00(t, 2H), 4.27(t, 2H),<br>6.80(d, 2H), 7.37(d, 2H) |
| 5.50 | Propyl | Tetrahydropyran-3-yl | 4-Br | 3.90(m, 2H), 4.00(t, 2H), 4.27(t, 2H),<br>6.80(d, 2H), 7.37(d, 2H) |
| 5.51 | Ethyl | Tetrahydropyran-4-yl | 4-Br | 3.90–4.10(m, 4H), 4.27(t, 2H),<br>6.80(d, 2H), 7.37(d, 2H) |
| 5.52 | Propyl | Tetrahydropyran-4-yl | 4-Br | 3.90–4.10(m, 4H), 4.27(t, 2H),<br>6.80(d, 2H), 7.37(d, 2H) |
| 5.53 | Ethyl | Tetrahydrothiopyran-4-yl | 4-Br | 4.00(t, 2H), 4.27(t, 2H), 6.80(d, 2H),<br>7.37(d, 2H) |
| 5.54 | Propyl | Tetrahydrothiopyran-4-yl | 4-Br | 4.00(t, 2H), 4.27(t, 2H), 6.80(d, 2H),<br>7.37(d, 2H) |

TABLE 6

XI ($R^e = -CH_2CH_2CH_2-S-\phi$ ; $R^g$, $R^h$, $R^i = H$)

| No. | $R^d$ | $R^f$ | Radicals on phenyl ring | phys. data/$^1$H-NMR [δ in ppm], mp. [°C.] |
|---|---|---|---|---|
| 6.01 | Ethyl | Tetrahydropyran-3-yl | — | 3.90(m, 2H), 4.17(t, 2H), 7.10–7.40(m, 5H) |
| 6.02 | Propyl | Tetrahydropyran-3-yl | — | 3.90(m, 2H), 4.17(t, 2H), 7.10–7.40(m, 5H) |
| 6.03 | Ethyl | Tetrahydropyran-4-yl | — | 4.00(m, 2H), 4.17(t, 2H), 7.10–7.40(m, 5H) |
| 6.04 | Propyl | Tetrahydropyran-4-yl | — | 4.00(m, 2H), 4.17(t, 2H), 7.10–7.40(m, 5H) |
| 6.05 | Ethyl | Tetrahydrothiopyran-3-yl | — | 4.17(t, 2H), 7.10–7.40(m, 5H) |
| 6.06 | Propyl | Tetrahydrothiopyran-3-yl | — | 4.17(t, 2H), 7.10–7.40(m, 5H) |
| 6.07 | Ethyl | Tetrahydropyran-3-yl | 4-F | 3.90(m, 2H), 4.17(t, 2H), 7.00(t, 2H),<br>7.33(m, 2H) |
| 6.08 | Propyl | Tetrahydropyran-3-yl | 4-F | 3.90(m, 2H), 4.17(t, 2H), 7.00(t, 2H),<br>7.33(m, 2H) |
| 6.09 | Ethyl | Tetrahydropyran-4-yl | 4-F | 4.00(m, 2H), 4.17(t, 2H), 7.00(t, 2H),<br>7.33(m, 2H) |
| 6.10 | Propyl | Tetrahydropyran-4-yl | 4-F | 4.00(m, 2H), 4.17(t, 2H), 7.00(t, 2H),<br>7.33(m, 2H) |
| 6.11 | Ethyl | Tetrahydrothiopyran-3-yl | 4-F | 4.17(t, 2H), 7.00(t, 2H), 7.33(m, 2H) |
| 6.12 | Propyl | Tetrahydrothiopyran-3-yl | 4-F | 4.17(t, 2H), 7.00(t, 2H), 7.33(m, 2H) |
| 6.13 | Ethyl | Tetrahydropyran-3-yl | 4-Cl | 3.90(m, 2H), 4.17(t, 2H), 7.27(s, 4H) |
| 6.14 | Propyl | Tetrahydropyran-3-yl | 4-Cl | 3.90(m, 2H), 4.17(t, 2H), 7.27(s, 4H) |
| 6.15 | Ethyl | Tetrahydropyran-4-yl | 4-Cl | 4.00(m, 2H), 4.17(t, 2H), 7.27(s, 4H) |
| 6.16 | Propyl | Tetrahydropyran-4-yl | 4-Cl | 4.00(m, 2H), 4.17(t, 2H), 7.27(s, 4H) |
| 6.17 | Ethyl | Tetrahydrothiopyran-3-yl | 4-Cl | 4.17(t, 2H), 7.27(s, 4H) |
| 6.18 | Propyl | Tetrahydrothiopyran-3-yl | 4-Cl | 4.17(t, 2H), 7.27(s, 4H) |
| 6.19 | Ethyl | Tetrahydropyran-3-yl | 2-Cl | 3.90(m, 2H), 4.20(t, 2H), 7.07–7.40(m, 4H) |
| 6.20 | Propyl | Tetrahydropyran-3-yl | 2-Cl | 3.90(m, 2H), 4.20(t, 2H), 7.07–7.40(m, 4H) |
| 6.21 | Ethyl | Tetrahydropyran-4-yl | 2-Cl | 4.00(m, 2H), 4.20(t, 2H), 7.07–7.40(m, 4H) |
| 6.22 | Propyl | Tetrahydropyran-4-yl | 2-Cl | 4.00(m, 2H), 4.20(t, 2H), 7.07–7.40(m, 4H) |
| 6.23 | Ethyl | Tetrahydrothiopyran-3-yl | 2-Cl | 4.20(t, 2H), 7.07–7.40(m, 4H) |
| 6.24 | Propyl | Tetrahydrothiopyran-3-yl | 2-Cl | 4.20(t, 2H), 7.07–7.40(m, 4H) |
| 6.25 | Ethyl | Tetrahydropyran-3-yl | 3-Cl | 3.90(m, 2H), 4.20(t, 2H), 7.17(m, 3H)<br>7.30(m, 1H) |
| 6.26 | Propyl | Tetrahydropyran-3-yl | 3-Cl | 3.90(m, 2H), 4.20(t, 2H), 7.17(m, 3H)<br>7.30(m, 1H) |
| 6.27 | Ethyl | Tetrahydropyran-4-yl | 3-Cl | 4.00(m, 2H), 4.20(t, 2H), 7.17(m, 3H)<br>7.30(m, 1H) |

TABLE 6-continued

| No. | $R^d$ | $R^f$ | Radicals on phenyl ring | phys. data/$^1$H-NMR [δ in ppm], mp. [°C.] |
|---|---|---|---|---|
| 6.28 | Propyl | Tetrahydropyran-4-yl | 3-Cl | 4.00(m, 2H), 4.20(t, 2H), 7.17(m, 3H) 7.30(m, 1H) |
| 6.29 | Ethyl | Tetrahydrothiopyran-3-yl | 3-Cl | 4.20(t, 2H), 7.17(m, 3H), 7.30(m, 1H) |
| 6.30 | Propyl | Tetrahydrothiopyran-3-yl | 3-Cl | 4.20(t, 2H), 7.17(m, 3H), 7.30(m, 1H) |
| 6.31 | Ethyl | Tetrahydropyran-3-yl | 2,5-$Cl_2$ | 3.90(m, 2H), 4.20(t, 2H), 7.07(dd, 1H), 7.20(d, 1H) 7.30(d, 1H) |
| 6.32 | Propyl | Tetrahydropyran-3-yl | 2,5-$Cl_2$ | 3.90(m, 2H), 4.20(t, 2H), 7.07(dd, 1H), 7.20(d, 1H) 7.30(d, 1H) |
| 6.33 | Ethyl | Tetrahydropyran-4-yl | 2,5-$Cl_2$ | 4.00(m, 2H), 4.20(t, 2H), 7.07(dd, 1H), 7.20(d, 1H) 7.30(d, 1H) |
| 6.34 | Propyl | Tetrahydropyran-4-yl | 2,5-$Cl_2$ | 4.00(m, 2H), 4.20(t, 2H), 7.07(dd, 1H), 7.20(d, 1H) 7.30(d, 1H) |
| 6.35 | Ethyl | Tetrahydrothiopyran-3-yl | 2,5-$Cl_2$ | 4.20(t, 2H), 7.07(dd, 1H), 7.20(d, 1H) 7.30(d, 1H) |
| 6.36 | Propyl | Tetrahydrothiopyran-3-yl | 2,5-$Cl_2$ | 4.20(t, 2H), 7.07(dd, 1H), 7.20(d, 1H) 7.30(d, 1H) |
| 6.37 | Ethyl | Tetrahydropyran-3-yl | 2,6-$Cl_2$ | 3.90(m, 2H), 4.20(t, 2H), 7.20(t, 1H) 7.40(d, 2H) |
| 6.38 | Propyl | Tetrahydropyran-3-yl | 2,6-$Cl_2$ | 3.90(m, 2H), 4.20(t, 2H), 7.20(t, 1H) 7.40(d, 2H) |
| 6.39 | Ethyl | Tetrahydropyran-4-yl | 2,6-$Cl_2$ | 4.00(m, 2H), 4.20(t, 2H), 7.20(t, 1H) 7.40(d, 2H) |
| 6.40 | Propyl | Tetrahydropyran-4-yl | 2,6-$Cl_2$ | 4.00(m, 2H), 4.20(t, 2H), 7.20(t, 1H) 7.40(d, 2H) |
| 6.41 | Ethyl | Tetrahydrothiopyran-3-yl | 2,6-$Cl_2$ | 4.20(t, 2H), 7.20(t, 1H), 7.40(d, 2H) |
| 6.42 | Propyl | Tetrahydrothiopyran-3-yl | 2,6-$Cl_2$ | 4.20(t, 2H), 7.20(t, 1H), 7.40(d, 2H) |

TABLE 7

| No. | $R^d$ | $R^f$ | Radicals on phenyl ring | phys. data/$^1$H-NMR [δ in ppm], mp. [°C.] |
|---|---|---|---|---|
| 7.01 | Ethyl | Tetrahydropyran-3-yl | — | 3.90(m, 2H), 4.25(t, 2H), 4.58(s, 2H), 7.38(s, 5H) |
| 7.02 | Propyl | Tetrahydropyran-3-yl | — | 3.90(m, 2H), 4.25(t, 2H), 4.58(s, 2H), 7.38(s, 5H) |
| 7.03 | Ethyl | Tetrahydropyran-4-yl | — | 4.03(m, 2H), 4.33(m, 2H), 4.60(s, 2H), 7.40(s, 5H) |
| 7.04 | Propyl | Tetrahydropyran-4-yl | — | 4.03(m, 2H), 4.33(m, 2H), 4.60(s, 2H), 7.40(s, 5H) |
| 7.05 | Ethyl | Tetrahydrothiopyran-3-yl | — | 4.27(s, 2H), 4.57(s, 2H), 7.35(s, 5H) |
| 7.06 | Propyl | Tetrahydrothiopyran-3-yl | — | 4.27(m, 2H), 4.57(s, 2H), 7.35(s, 5H) |
| 7.07 | Ethyl | Tetrahydropyran-3-yl | 2-F | 3.93(m, 2H), 4.27(m, 2H), 4.67(s, 2H), 6.93–7.50(m, 4H) |
| 7.08 | Propyl | Tetrahydropyran-3-yl | 2-F | 3.93(m, 2H), 4.27(m, 2H), 4.67(s, 2H), 6.93–7.50(m, 4H) |
| 7.09 | Ethyl | Tetrahydropyran-4-yl | 2-F | 4.03(m, 2H), 4.27(m, 2H), 4.63(s, 2H), 6.97–7.50(m, 4H) |
| 7.10 | Propyl | Tetrahydropyran-4-yl | 2-F | 4.03(m, 2H), 4.27(m, 2H), 4.63(s, 2H), 6.97–7.50(m, 4H) |
| 7.11 | Ethyl | Tetrahydrothiopyran-3-yl | 2-F | 4.27(m, 2H), 4.67(s, 2H), 6.97–7.50(m, 4H) |
| 7.12 | Propyl | Tetrahydrothiopyran-3-yl | 2-F | 4.27(m, 2H), 4.67(s, 2H), 6.97–7.50(m, 4H) |
| 7.13 | Ethyl | Tetrahydropyran-3-yl | 3-F | 3.93(m, 2H), 4.27(m, 2H), 4.57(s, 2H), 6.90–7.15(m, 3H), 7.23–7.40(m, 1H) |
| 7.14 | Propyl | Tetrahydropyran-3-yl | 3-F | 3.93(m, 2H), 4.27(m, 2H), 4.57(s, 2H), 6.90–7.15(m, 3H), 7.23–7.40(s, 1H) |
| 7.15 | Ethyl | Tetrahydropyran-4-yl | 3-F | 4.03(m, 2H), 4.25(m, 2H), 4.60(s, 2H), |

TABLE 7-continued

| No. | $R^d$ | $R^f$ | Radicals on phenyl ring | phys. data/$^1$H-NMR [δ in ppm], mp. [°C.] |
|---|---|---|---|---|
| 7.16 | Propyl | Tetrahydropyran-4-yl | 3-F | 6.90–7.18(m, 3H), 7.26–7.40(m, 1H) 4.03(m, 2H), 4.25(m, 2H), 4.60(s, 2H), 6.90–7.18(m, 3H), 7.26–7.40(m, 1H) |
| 7.17 | Ethyl | Tetrahydrothiopyran-3-yl | 3-F | 4.27(m, 2H), 4.60(s, 2H), 6.90–7.15(m, 3H), 7.23–7.40(m, 1H) |
| 7.18 | Propyl | Tetrahydrothiopyran-3-yl | 3-F | 4.27(m, 2H), 4.60(s, 2H), 6.90–7.15(m, 3H), 7.23–7.40(m, 1H) |
| 7.19 | Ethyl | Tetrahydropyran-3-yl | 4-F | 3.93(m, 2H), 4.23(m, 2H), 4.53(s, 2H), 7.00(m, 2H), 7.30(m, 2H) |
| 7.20 | Propyl | Tetrahydropyran-3-yl | 4-F | 3.93(m, 2H), 4.23(m, 2H), 4.53(s, 2H), 7.00(m, 2H), 7.30(m, 2H) |
| 7.21 | Ethyl | Tetrahydropyran-4-yl | 4-F | 92 |
| 7.22 | Propyl | Tetrahydropyran-4-yl | 4-F | 4.00(m, 2H), 4.23(m, 2H), 4.53(s, 2H), 7.03(m, 2H), 7.30(m, 2H) |
| 7.23 | Ethyl | Tetrahydrothiopyran-3-yl | 4-F | 4.27(m, 2H), 4.53(s, 2H), 7.03(m, 2H), 7.30(m, 2H) |
| 7.24 | Propyl | Tetrahydrothiopyran-3-yl | 4-F | 4.27(m, 2H), 4.53(s, 2H), 7.03(m, 2H), 7.30(m, 2H) |
| 7.25 | Ethyl | Tetrahydropyran-3-yl | 2-Cl | |
| 7.26 | Propyl | Tetrahydropyran-3-yl | 2-Cl | |
| 7.27 | Ethyl | Tetrahydropyran-4-yl | 2-Cl | |
| 7.28 | Propyl | Tetrahydropyran-4-yl | 2-Cl | |
| 7.29 | Ethyl | Tetrahydrothiopyran-3-yl | 2-Cl | |
| 7.30 | Propyl | Tetrahydrothiopyran-3-yl | 2-Cl | |
| 7.31 | Ethyl | Tetrahydropyran-3-yl | 3-Cl | |
| 7.32 | Propyl | Tetrahydropyran-3-yl | 3-Cl | |
| 7.33 | Ethyl | Tetrahydropyran-4-yl | 3-Cl | |
| 7.34 | Propyl | Tetrahydropyran-4-yl | 3-Cl | |
| 7.35 | Ethyl | Tetrahydrothiopyran-3-yl | 3-Cl | |
| 7.36 | Propyl | Tetrahydrothiopyran-3-yl | 3-Cl | |
| 7.37 | Ethyl | Tetrahydropyran-3-yl | 4-Cl | 3.93(m, 2H), 4.27(m, 2H), 4.53(s, 2H), 7.28(m, 4H) |
| 7.38 | Propyl | Tetrahydropyran-3-yl | 4-Cl | 3.93(m, 2H), 4.27(m, 2H), 4.53(s, 2H), 7.28(m, 4H) |
| 7.39 | Ethyl | Tetrahydropyran-4-yl | 4-Cl | 67–72 |
| 7.40 | Propyl | Tetrahydropyran-4-yl | 4-Cl | 4.00(m, 2H), 4.23(m, 2H), 4.53(s, 2H), 7.28(m, 4H) |
| 7.41 | Ethyl | Tetrahydrothiopyran-3-yl | 4-Cl | 4.27(m, 2H), 4.53(s, 2H), 7.28(m, 4H) |
| 7.42 | Propyl | Tetrahydrothiopyran-3-yl | 4-Cl | 4.27(m, 2H), 4.53(s, 2H), 7.28(m, 4H) |
| 7.43 | Ethyl | Tetrahydropyran-3-yl | 2-CH$_3$ | 3.93(m, 2H), 4.23(m, 2H), 4.57(s, 2H), 7.09–7.33(m, 4H) |
| 7.44 | Propyl | Tetrahydropyran-3-yl | 2-CH$_3$ | 3.93(m, 2H), 4.23(m, 2H), 4.57(s, 2H), 7.09–7.33(m, 4H) |
| 7.45 | Ethyl | Tetrahydropyran-4-yl | 2-CH$_3$ | 4.00(m, 2H), 4.23(m, 2H), 4.57(s, 2H), 7.09–7.33(m, 4H) |
| 7.46 | Propyl | Tetrahydropyran-4-yl | 2-CH$_3$ | 4.00(m, 2H), 4.23(m, 2H), 4.57(s, 2H), 7.09–7.33(m, 4H) |
| 7.47 | Ethyl | Tetrahydrothiopyran-3-yl | 2-CH$_3$ | 4.23(m, 2H), 4.57(s, 2H), 7.09–7.33(m, 4H) |
| 7.48 | Propyl | Tetrahydrothiopyran-3-yl | 2-CH$_3$ | 4.23(m, 2H), 4.57(s, 2H), 7.09–7.33(m, 4H) |
| 7.49 | Ethyl | Tetrahydropyran-3-yl | 3-CH$_3$ | 3.93(m, 2H), 4.25(m, 2H), 4.57(s, 2H), 7.00–7.32(m, 4H) |
| 7.50 | Propyl | Tetrahydropyran-3-yl | 3-CH$_3$ | 3.93(m, 2H), 4.25(m, 2H), 4.57(s, 2H), 7.00–7.32(m, 4H) |
| 7.51 | Ethyl | Tetrahydropyran-4-yl | 3-CH$_3$ | 4.00(m, 2H), 4.27(m, 2H), 4.57(s, 2H), 7.00–7.32(m, 4H) |
| 7.52 | Propyl | Tetrahydropyran-4-yl | 3-CH$_3$ | 4.00(m, 2H), 4.27(m, 2H), 4.57(s, 2H), 7.00–7.32(m, 4H) |
| 7.53 | Ethyl | Tetrahydrothiopyran-3-yl | 3-CH$_3$ | 4.27(m, 2H), 4.60(s, 2H), 7.00–7.32(m, 4H) |
| 7.54 | Propyl | Tetrahydrothiopyran-3-yl | 3-CH$_3$ | 4.27(m, 2H), 4.60(s, 2H), 7.00–7.32(m, 4H) |
| 7.55 | Ethyl | Tetrahydropyran-3-yl | 4-CH$_3$ | 3.93(m, 2H), 4.20(m, 2H), 4.53(s, 2H), 7.07–7.30(m, 4H) |
| 7.56 | Propyl | Tetrahydropyran-3-yl | 4-CH$_3$ | 3.93(m, 2H), 4.20(m, 2H), 4.53(s, 2H), 7.07–7.30(m, 4H) |

TABLE 7-continued

XI ($R^e = -CH_2CH_2OCH_2-\phenyl$ ; $R^g, R^h, R^i = H$)

| No. | $R^d$ | $R^f$ | Radicals on phenyl ring | phys. data/$^1$H-NMR [δ in ppm], mp. [°C.] |
|---|---|---|---|---|
| 7.57 | Ethyl | Tetrahydropyran-4-yl | 4-CH$_3$ | 4.00(m, 2H), 4.23(m, 2H), 4.57(s, 2H), 7.03–7.27(m, 4H) |
| 7.58 | Propyl | Tetrahydropyran-4-yl | 4-CH$_3$ | 4.00(m, 2H), 4.23(m, 2H), 4.57(s, 2H), 7.03–7.27(m, 4H) |
| 7.59 | Ethyl | Tetrahydrothiopyran-3-yl | 4-CH$_3$ | 4.23(m, 2H), 4.57(s, 2H), 7.07–7.30(m, 4H) |
| 7.60 | Propyl | Tetrahydrothiopyran-3-yl | 4-CH$_3$ | 4.28(m, 2H), 4.57(s, 2H), 7.07–7.30(m, 4H) |
| 7.61 | Ethyl | Tetrahydropyran-3-yl | 4-tert.-C$_4$H$_9$ | 3.93(m, 2H), 4.23(m, 2H), 4.53(s, 2H), 7.20–7.40(m, 4H) |
| 7.62 | Propyl | Tetrahydropyran-3-yl | 4-tert.-C$_4$H$_9$ | 3.93(m, 2H), 4.23(m, 2H), 4.53(s, 2H), 7.20–7.40(m, 4H) |
| 7.63 | Ethyl | Tetrahydropyran-4-yl | 4-tert.-C$_4$H$_9$ | 4.00(m, 2H), 4.23(m, 2H), 4.53(s, 2H), 7.20–7.40(m, 4H) |
| 7.64 | Propyl | Tetrahydropyran-4-yl | 4-tert.-C$_4$H$_9$ | 4.00(m, 2H), 4.23(m, 2H), 4.53(s, 2H), 7.20–7.40(m, 4H) |
| 7.65 | Ethyl | Tetrahydrothiopyran-3-yl | 4-tert.-C$_4$H$_9$ | 4.23(m, 2H), 4.53(s, 2H), 7.20–7.40(m, 4H) |
| 7.66 | Propyl | Tetrahydrothiopyran-3-yl | 4-tert.-C$_4$H$_9$ | 4.23(m, 2H), 4.53(s, 2H), 7.20–7.40(m, 4H) |

TABLE 8

XI ($R^e = -CH_2CH_2-S-CH_2-\phenyl$ ; $R^g, R^h, R^i = H$)

| No. | $R^d$ | $R^f$ | Radicals on phenyl ring | phys. data/$^1$H—NMR [δ in ppm], mp. [°C.] |
|---|---|---|---|---|
| 8.01 | Ethyl | Tetrahydropyran-3-yl | — | 3.73(s, 2H), 3.90(m, 2H), 4.17(t, 2H), 7.28(s, 5H) |
| 8.02 | Propyl | Tetrahydropyran-3-yl | — | 3.73(s, 2H), 3.90(m, 2H), 4.17(t, 2H), 7.28(s, 5H) |
| 8.03 | Ethyl | Tetrahydropyran-4-yl | — | 3.77(s, 2H), 4.00(m, 2H), 4.13(t, 2H), 7.28(s, 5H) |
| 8.04 | Propyl | Tetrahydropyran-4-yl | — | 3.77(s, 2H), 4.00(m, 2H), 4.13(t, 2H), 7.28(s, 5H) |
| 8.05 | Ethyl | Tetrahydrothiopyran-3-yl | — | 3.80(s, 2H), 4.13(t, 2H), 7.28(s, 5H) |
| 8.06 | Propyl | Tetrahydrothiopyran-3-yl | — | 3.80(s, 2H), 4.13(t, 2H), 7.28(s, 5H) |
| 8.07 | Ethyl | Tetrahydropyran-3-yl | 4-F | 3.72(s, 2H), 3.90(m, 2H), 4.13(t, 2H), 7.00(m, 2H), 7.30(m, 2H) |
| 8.08 | Propyl | Tetrahydropyran-3-yl | 4-F | 3.72(s, 2H), 3.90(m, 2H), 4.13(t, 2H), 7.00(m, 2H), 7.30(m, 2H) |
| 8.09 | Ethyl | Tetrahydropyran-4-yl | 4-F | 63–65 |
| 8.10 | Propyl | Tetrahydropyran-4-yl | 4-F | 3.73(s, 2H), 4.00(m, 2H), 4.13(t, 2H), 7.00(m, 2H), 7.30(m, 2H) |
| 8.11 | Ethyl | Tetrahydrothiopyran-3-yl | 4-F | 3.75(s, 2H), 4.13(t, 2H), 7.00(m, 2H), 7.30(m, 2H) |
| 8.12 | Propyl | Tetrahydrothiopyran-3-yl | 4-F | 3.75(s, 2H), 4.13(t, 2H), 7.00(m, 2H), 7.30(m, 2H) |
| 8.13 | Ethyl | Tetrahydropyran-3-yl | 4-Cl | 3.77(s, 2H), 3.93(m, 2H), 4.13(t, 2H), 7.30(s, 4H) |
| 8.14 | Propyl | Tetrahydropyran-3-yl | 4-Cl | 3.77(s, 2H), 3.93(m, 2H), 4.13(t, 2H), 7.30(s, 4H) |
| 8.15 | Ethyl | Tetrahydropyran-4-yl | 4-Cl | 3.73(s, 2H), 4.00(m, 2H), 4.17(t, 2H), 7.30(s, 4H) |
| 8.16 | Propyl | Tetrahydropyran-4-yl | 4-Cl | 3.73(s, 2H), 4.00(m, 2H), 4.17(t, 2H), 7.30(s, 4H) |
| 8.17 | Ethyl | Tetrahydrothiopyran-3-yl | 4-Cl | 3.73(s, 2H), 4.13(m, 2H), 7.30(s, 4H) |
| 8.18 | Propyl | Tetrahydrothiopyran-3-yl | 4-Cl | 3.73(s, 2H), 4.13(m, 2H), 7.30(s, 4H) |

TABLE 9

Structure: cyclohexanedione with OH, R^f, NO—CH₂CH₂CH₂CH₂—O—phenyl, R^d substituents XI (R^e = —CH₂CH₂CH₂CH₂—O—phenyl ; R^g, R^h, R^i = H)

| No. | R^d | R^f | Radicals on phenyl ring | phys. data/$^1$H—NMR [δ in ppm], mp. [°C.] |
|---|---|---|---|---|
| 9.01 | Ethyl | Tetrahydropyran-3-yl | — | 3.70–4.20(m, 6H), 6.90(m, 3H), 7.30(m, 2H) |
| 9.02 | Propyl | Tetrahydropyran-3-yl | — | 3.70–4.20(m, 6H), 6.90(m, 3H), 7.30(m, 2H) |
| 9.03 | Ethyl | Tetrahydropyran-4-yl | — | 3.83–4.23(m, 6H), 6.90(m, 3H), 7.30(m, 2H) |
| 9.04 | Propyl | Tetrahydropyran-4-yl | — | 3.83–4.23(m, 6H), 6.90(m, 3H), 7.30(m, 2H) |
| 9.05 | Ethyl | Tetrahydrothiopyran-3-yl | — | 4.00(bs, 2H), 4.13(bs, 2H), 6.90(m, 3H) 7.30(m, 2H) |
| 9.06 | Propyl | Tetrahydrothiopyran-3-yl | — | 4.00(bs, 2H), 4.13(bs, 2H), 6.90(m, 3H) 7.30(m, 2H) |
| 9.07 | Ethyl | Tetrahydropyran-3-yl | 2-F | 3.93(m, 2H), 4.00–4.20(m, 4H), 6.80–7.15(m, 4H) |
| 9.08 | Propyl | Tetrahydropyran-3-yl | 2-F | 3.93(m, 2H), 4.00–4.20(m, 4H), 6.08–7.15(m, 4H) |
| 9.09 | Ethyl | Tetrahydropyran-4-yl | 2-F | 68–72 |
| 9.10 | Propyl | Tetrahydropyran-4-yl | 2-F | 3.90–4.20(m, 6H), 6.80–7.15(m, 4H) |
| 9.11 | Ethyl | Tetrahydrothiopyran-3-yl | 2-F | 4.00–4.20(m, 4H), 6.80–7.15(m, 4H) |
| 9.12 | Propyl | Tetrahydrothiopyran-3-yl | 2-F | 4.00–4.20(m, 4H), 6.80–7.15(m, 4H) |
| 9.13 | Ethyl | Tetrahydropyran-3-yl | 3-F | |
| 9.14 | Propyl | Tetrahydropyran-3-yl | 3-F | |
| 9.15 | Ethyl | Tetrahydropyran-4-yl | 3-F | |
| 9.16 | Propyl | Tetrahydropyran-4-yl | 3-F | |
| 9.17 | Ethyl | Tetrahydrothiopyran-3-yl | 3-F | |
| 9.18 | Propyl | Tetrahydrothiopyran-3-yl | 3-F | |
| 9.19 | Ethyl | Tetrahydropyran-3-yl | 4-F | 3.80–4.20(m, 6H), 6.75–7.05(m, 4H) |
| 9.20 | Propyl | Tetrahydropyran-3-yl | 4-F | 3.80–4.20(m, 6H), 6.75–7.05(m, 4H) |
| 9.21 | Ethyl | Tetrahydropyran-4-yl | 4-F | 3.90–4.20(m, 6H), 6.75–7.05(m, 4H) |
| 9.22 | Propyl | Tetrahydropyran-4-yl | 4-F | 3.90–4.20(s, 6H), 6.75–7.05(m, 4H) |
| 9.23 | Ethyl | Tetrahydrothiopyran-3-yl | 4-F | 3.90–4.20(m, 4H), 6.75–7.05(m, 4H) |
| 9.24 | Propyl | Tetrahydrothiopyran-3-yl | 4-F | 3.90–4.20(m, 4H), 6.75–7.05(m, 4H) |
| 9.25 | Ethyl | Tetrahydropyran-3-yl | 4-Cl | 3.80–4.20(m, 6H), 6.80(m, 2H), 7.20(m, 2H) |
| 9.26 | Propyl | Tetrahydropyran-3-yl | 4-Cl | 3.80–4.20(m, 6H), 6.80(m, 2H), 7.20(m, 2H) |
| 9.27 | Ethyl | Tetrahydropyran-4-yl | 4-Cl | 3.90–4.20(m, 6H), 6.80(m, 2H), 7.20(m, 2H) |
| 9.28 | Propyl | Tetrahydropyran-4-yl | 4-Cl | 3.90–4.20(m, 6H), 6.80(m, 2H), 7.20(m, 2H) |
| 9.29 | Ethyl | Tetrahydrothiopyran-3-yl | 4-Cl | 3.90–4.20(m, 4H), 6.80(m, 2H), 7.20(m, 2H) |
| 9.30 | Propyl | Tetrahydrothiopyran-3-yl | 4-Cl | 3.90–4.20(m, 4H), 6.80(m, 2H), 7.20(m, 2H) |
| 9.31 | Ethyl | Tetrahydropyran-3-yl | 2,6-Cl$_2$ | 3.93(m, 2H), 4.00–4.25(m, 4H), 7.00(t, 1H), 7.30(d, 2H) |
| 9.32 | Propyl | Tetrahydropyran-3-yl | 2,6-Cl$_2$ | 3.93(m, 2H), 4.00–4.25(m, 4H), 7.00(t, 1H), 7.30(d, 2H) |
| 9.33 | Ethyl | Tetrahydropyran-4-yl | 2,6-Cl$_2$ | 3.90–4.25(m, 6H), 7.00(t, 1H), 7.30(d, 2H) |
| 9.34 | Propyl | Tetrahydropyran-4-yl | 2,6-Cl$_2$ | 3.90–4.25(m, 6H), 7.00(t, 1H), 7.30(d, 2H) |
| 9.35 | Ethyl | Tetrahydrothiopyran-3-yl | 2,6-Cl$_2$ | 4.00–4.20(m, 4H), 7.00(t, 1H), 7.30(d, 2H) |
| 9.36 | Propyl | Tetrahydrothiopyran-3-yl | 2,6-Cl$_2$ | 4.00–4.20(m, 4H), 7.00(t, 1H), 7.30(d, 2H) |

TABLE 10

Structure: cyclohexanedione with OH, R^f, NO—CH₂CH₂—O—CH₂CH₂—phenyl, R^d substituents XI (R^e = —CH₂CH₂—O—CH₂CH₂—phenyl ; R^g, R^h, R^i = H)

| No. | $R^d$ | $R^f$ | Radicals on phenyl ring | phys. data/$^1$H—NMR [δ in ppm], mp. [°C.] |
|---|---|---|---|---|
| 10.01 | Ethyl | Tetrahydropyran-3-yl | — | 3.90(m, 2H), 4.20(m, 2H), 7.25(m, 5H) |
| 10.02 | Propyl | Tetrahydropyran-3-yl | — | 3.90(m, 2H), 4.20(m, 2H), 7.25(m, 5H) |
| 10.03 | Ethyl | Tetrahydropyran-4-yl | — | |
| 10.04 | Propyl | Tetrahydropyran-4-yl | — | |
| 10.05 | Ethyl | Tetrahydrothiopyran-3-yl | — | 4.20(m, 2H), 7.25(m, 5H) |
| 10.06 | Propyl | Tetrahydrothiopyran-3-yl | — | 4.20(m, 2H), 7.25(m, 5H) |
| 10.07 | Ethyl | Tetrahydropyran-3-yl | 4-F | 3.90(m, 2H), 4.17(m, 2H), 6.93(m, 2H), 7.13(m, 2H) |
| 10.08 | Propyl | Tetrahydropyran-3-yl | 4-F | 3.90(m, 2H), 4.17(m, 2H), 6.93(m, 2H), 7.13(m, 2H) |
| 10.09 | Ethyl | Tetrahydropyran-4-yl | 4-F | |
| 10.10 | Propyl | Tetrahydropyran-4-yl | 4-F | |
| 10.11 | Ethyl | Tetrahydrothiopyran-3-yl | 4-F | 4.17(m, 2H), 6.93(m, 2H), 7.13(m, 2H) |
| 10.12 | Propyl | Tetrahydrothiopyran-3-yl | 4-F | 4.17(m, 2H), 6.93(m, 2H), 7.13(m, 2H) |
| 10.13 | Ethyl | Tetrahydropyran-3-yl | 4-Cl | 3.90(m, 2H), 4.17(m, 2H), 7.13(m, 4H) |
| 10.14 | Propyl | Tetrahydropyran-3-yl | 4-Cl | 3.90(m, 2H), 4.17(m, 2H), 7.13(m, 4H) |
| 10.15 | Ethyl | Tetrahydropyran-4-yl | 4-Cl | |
| 10.16 | Propyl | Tetrahydropyran-4-yl | 4-Cl | |
| 10.17 | Ethyl | Tetrahydrothiopyran-3-yl | 4-Cl | 4.17(m, 2H), 7.13(m, 4H) |
| 10.18 | Propyl | Tetrahydrothiopyran-3-yl | 4-Cl | 4.17(m, 2H), 7.13(m, 4H) |

TABLE 11

| No. | $R^d$ | $R^f$ | Radicals on phenyl ring | phys. data/$^1$H—NMR [δ in ppm], mp. [°C.] |
|---|---|---|---|---|
| 11.01 | Ethyl | Tetrahydropyran-3-yl | — | 3.80–4.17(m, 6H), 6.90(m, 3H), 7.27(m, 2H) |
| 11.02 | Propyl | Tetrahydropyran-3-yl | — | 3.80–4.17(m, 6H), 6.90(m, 3H), 7.27(m, 2H) |
| 11.03 | Ethyl | Tetrahydropyran-4-yl | — | 3.90–4.17(m, 6H), 6.90(m, 3H), 7.27(m, 2H) |
| 11.04 | Propyl | Tetrahydropyran-4-yl | — | 3.90–4.17(m, 6H), 6.90(m, 3H), 7.27(m, 2H) |
| 11.05 | Ethyl | Tetrahydrothiopyran-3-yl | — | 3.97(t, 2H), 4.07(t, 2H), 6.90(m, 3H), 7.27(m, 2H) |
| 11.06 | Propyl | Tetrahydrothiopyran-3-yl | — | 3.97(t, 2H), 4.07(t, 2H), 6.90(m, 3H), 7.27(m, 2H) |
| 11.07 | Ethyl | Tetrahydropyran-3-yl | 4-F | 3.90(m, 4H), 4.03(t, 2H), 6.70–7.03(m, 4H) |
| 11.08 | Propyl | Tetrahydropyran-3-yl | 4-F | 3.90(m, 4H), 4.03(t, 2H), 6.70–7.03(m, 4H) |
| 11.09 | Ethyl | Tetrahydropyran-4-yl | 4-F | 3.83–4.13(m, 6H), 6.70–7.03(m, 4H) |
| 11.10 | Propyl | Tetrahydropyran-4-yl | 4 F | 3.83–4.13(m, 6H), 6.70–7.03(m, 4H) |
| 11.11 | Ethyl | Tetrahydrothiopyran-3-yl | 4-F | 3.90(t, 2H), 4.03(t, 2H) 6.70–7.03(m, 4H) |
| 11.12 | Propyl | Tetrahydrothiopyran 3-yl | 4-F | 3.90(t, 2H), 4.03(t, 2H) 6.70–7.03(m, 4H) |
| 11.13 | Ethyl | Tetrahydropyran-3-yl | 4-Cl | 3.80–4.10(m, 6H), 6.80(d, 2H), 7.20(d, 2H) |
| 11.14 | Propyl | Tetrahydropyran-3-yl | 4-Cl | 3.80–4.10(m, 6H), 6.80(m, 2H), 7.20(d, 2H) |
| 11.15 | Ethyl | Tetrahydropyran-4-yl | 4-Cl | 3.87–4.10(m, 6H), 6.80(d, 2H), 7.20(d, 2H) |
| 11.16 | Propyl | Tetrahydropyran-4-yl | 4-Cl | 3.87–4.10(m, 6H), 6.80(d, 2H), 7.20(d, 2H) |
| 11.17 | Ethyl | Tetrahydrothiopyran-3-yl | 4-Cl | 54–61 |
| 11.18 | Propyl | Tetrahydrothiopyran-3-yl | 4-Cl | 3.90(t, 2H), 4.07(t, 2H), 6.80(d, 2H) 7.20(d, 2H) |

TABLE 12

| No. | $R^d$ | $R^e$ | $R^f$ | $R^g$ | $R^h$ | $R^i$ | Reference |
|---|---|---|---|---|---|---|---|
| 12.1 | $C_3H_7$ | $CH_2CH=CH_2$ | $CH_3$ | $CH_3$ | $CO_2CH_3$ | Na | DE-A 2 439 104 |
| 12.2 | $C_3H_7$ | $CH_2CH_3$ | $CH_2CH(CH_3)SCH_2CH_3$ | H | H | H | DE-A 2 822 304 |
| 12.3 | $C_2H_5$ | $CH_2CH=CHCl$ | $CH_2CH(CH_3)SCH_2CH_3$ | H | H | H | US-A 4 440 566 |
| 12.4 | $C_3H_7$ | $CH_2CH=CHCl$ | $CH_2CH(CH_3)SCH_2CH_3$ | H | H | H | US-A 4 440 566 |

TABLE 12-continued

XI

Structure: cyclohexenone with $OR^i$, $=NOR^e$, $R^d$, $R^f$, $R^g$, $R^h$ substituents and C=O.

| No. | $R^d$ | $R^e$ | $R^f$ | $R^g$ | $R^h$ | $R^i$ | Reference |
|---|---|---|---|---|---|---|---|
| 12.5 | $C_3H_7$ | $C_2H_5$ | 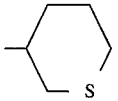 tetrahydrothiopyran-4-yl | H | H | H | EP-A 71 707 |
| 12.6 | $C_2H_5$ | $C_2H_5$ | 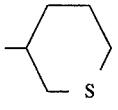 tetrahydrothiopyran-4-yl | H | H | H | EP-A 71 707 |
| 12.7 | $CH_3$ | $CH_2CH=CHCH_3$ | 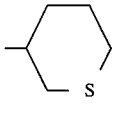 tetrahydrothiopyran-4-yl | H | H | H | EP-A 71 707 |
| 12.8 | $C_3H_7$ | $C_2H_5$ | 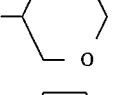 tetrahydropyran-4-yl | H | H | H | EP-A 71-707 |
| 12.9 | $C_2H_5$ | $CH_2CH=CHCl$ | 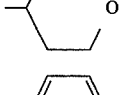 tetrahydropyran-4-yl | H | H | H | EP-A 142 741 |
| 12.10 | $C_3H_7$ | $C_2H_5$ | 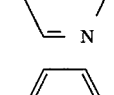 pyridin-4-yl | H | H | H | EP-A 66 195 |
| 12.11 | $C_2H_5$ | $C_2H_5$ | 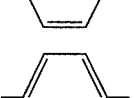 4-methylphenyl | H | H | H | DE-A 24 39 104 |
| 12.12 | $C_2H_5$ | $CH_2CH=CHCH_3$ | 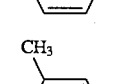 4-ethylphenyl | H | H | H | DE-A 38 08 072 |
| 12.13 | $C_2H_5$ | $C_2H_5$ | 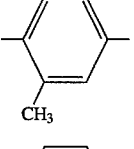 2,4,6-trimethylphenyl | H | H | H | EP-A 880 301 |
| 12.14 | $C_3H_7$ | $CH_2CH=CHCl$ | 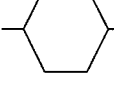 4-methylcyclohexyl | H | H | H | EP-A 88 299 |
| 12.15 | $C_3H_7$ | $CH_2CH=CHCH_3$ | 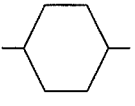 4-methylcyclohexyl | H | H | H | EP-A 88 299 |
| 12.16 | $C_2H_5$ | $CH_2CH=CHCH_3$ | 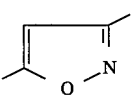 3-isopropyl-5-methylisoxazol-4-yl | H | H | H | EP-A 238 021 |

TABLE 12-continued

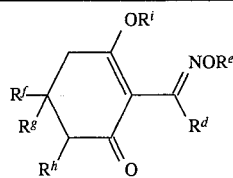

XI

| No. | $R^d$ | $R^e$ | $R^f$ | $R^g$ | $R^h$ | $R^i$ | Reference |
|---|---|---|---|---|---|---|---|
| 12.17 | $C_3H_7$ | $CH_2CH=CHCH_3$ | 3-isopropyl-5-methylisoxazol-4-yl | H | H | H | EP-A 238 021 |
| 12.18 | $C_2H_5$ | $CH_2CH=CHCl$ | 4-(propargyloxymethyl)phenyl | H | H | H | EP-A 137 174 |
| 12.19 | $C_3H_7$ | $C_2H_5$ | 4-(ethoxymethyl)phenyl | H | H | H | EP-A 2 137 200 |
| 12.20 | $C_3H_7$ | $C_2H_5$ | 3,4-dibromotetrahydropyran-4-yl | H | H | H | EP-A 230 235 |
| 12.21 | $C_3H_7$ | $CH_2CH=CHCl$ | 3,4-dibromotetrahydropyran-4-yl | H | H | H | EP-A 230 235 |
| 12.22 | $C_3H_7$ | $CH_2CH=CHCl$ | 2,6,6-trimethylcyclohex-1-enyl | H | H | H | EP-A 46 860 |
| 12.23 | $C_3H_7$ | $C_2H_5$ | cyclohexyl | H | H | H | JP-A 540 191 945 |
| 12.24 | $C_3H_7$ | $C_2H_5$ | cyclohex-1-enyl | H | H | H | EP-A 46 860 |
| 12.25 | $CH_3$ | $CH_2CH=CHCl$ | 4-methylcyclohexyl | H | H | H | EP-A 88 299 |
| 12.26 | $C_3H_7$ | $C_2H_5$ | 4-(trifluoromethyl)phenyl | H | H | K | EP-A 137 174 |
| 12.27 | $C_2H_5$ | $CH_2CH=CHCl$ | 2,6,6-trimethylcyclohex-1-enyl | H | H | H | EP-A 46 860 |

TABLE 12-continued $$\text{XI}$$

Structure: cyclohexenone with OR$^i$ at position 4 (with CH$_2$), R$^f$ and R$^g$ at position 5, R$^h$ at position 6, C(=NOR$^e$)R$^d$ at position 2, C=O at position 1.

| No. | R$^d$ | R$^e$ | R$^f$ | R$^g$ | R$^h$ | R$^i$ | Reference |
|---|---|---|---|---|---|---|---|
| 12.28 | C$_3$H$_7$ | CH$_2$CH=CHCH$_3$ | 2-methyl-1,3-thiazol-5-yl (S–C(CH$_3$)=N–CH=CH–) | H | H | H | EP-A 125 094 |
| 12.29 | C$_3$H$_7$ | CH$_2$CH=CHCl | 2-methyl-1,3-thiazol-5-yl | H | H | H | EP-A 125 094 |
| 12.30 | C$_3$H$_7$ | C$_2$H$_5$ | 2,4,6-trimethylcyclohexyl | H | H | H | EP-A 88 299 |
| 12.31 | C$_3$H$_7$ | CH$_2$CH=CH$_2$ | 1-hydroxy-1,4-dimethyl-3-(ethylthio)cyclohexyl | H | H | H | EP-A 228 598 |
| 12.32 | C$_2$H$_5$ | C$_2$H$_5$ | 2,3-dihydroxy-5-methylcyclohexyl | H | H | H | EP-A 228 598 |
| 12.33 | C$_3$H$_7$ | C$_2$H$_5$ | 1,3-dimethyl-1H-pyrazol-4-yl | H | H | H | EP-A 66 195 |
| 12.34 | C$_3$H$_7$ | CH$_2$CH=CHCl | 1,3-dimethyl-1H-pyrrol-4-yl | H | H | H | EP-A 66195 |
| 12.35 | C$_3$H$_7$ | CH$_2$CH=CH$_2$ | 2-methyl-1,3-thiazol-5-yl | H | H | H | EP-A 125 094 |
| 12.36 | C$_3$H$_7$ | C$_3$H$_7$ | CH(SCH$_2$CH$_3$)$_2$ | H | H | H | EP-A 230 260 |
| 12.37 | C$_3$H$_7$ | C$_2$H$_5$ | 4-methyltetrahydrothiopyran-3-yl S-oxide | H | H | H | EP-A 115 808 |

TABLE 12-continued

Structure XI: cyclohexenone with substituents $OR^i$, $R^f$, $R^g$, $R^h$, and side chain $C(R^d)=NOR^e$

| No. | $R^d$ | $R^e$ | $R^f$ | $R^g$ | $R^h$ | $R^i$ | Reference |
|---|---|---|---|---|---|---|---|
| 12.38 | $C_3H_7$ | $C_2H_5$ | 3-methyl-tetrahydrothiopyranyl-1,1-dioxide | H | H | H | EP-A 115 808 |
| 12.39 | $C_3H_7$ | $C_2H_5$ | $CH_3$ | $CH_3$ | $C(CH_3)=NOCH_3$ | H | EP-A 172 551 |
| 12.40 | $C_3H_7$ | $CH_2CH=CH_2$ | 3-methyl-tetrahydrothiopyranyl-1,1-dioxide | OH | H | H | Proceedings Brit. Crop-Protection Conference-weeds 1985 vol. 1 pp. 93–98 |
| 12.41 | $C_2H_5$ | $CH_2CH=CH-CH_2-C_6H_4-Cl$ | tetrahydrothiopyranyl | H | H | H | EP-A 38 38 309 |
| 12.42 | $C_2H_5$ | $CH_2CH_2-CH=CH-C_6H_4-Cl$ | tetrahydrothiopyranyl | H | H | H | EP-A 38 38 309 |
| 12.43 | $C_2H_5$ | $CH_2CH_2-CH=CH-C_6H_4-F$ | tetrahydrothiopyranyl | H | H | H | EP-A 38 38 309 |
| 12.44 | $n-C_3H_7$ | $CH_2CH_2-CH=CH-C_6H_4-F$ | tetrahydrothiopyranyl | H | H | H | EP-A 38 38 309 |
| 12.45 | $C_2H_5$ | $CH_2CH=CH-CH_2-C_6H_5$ | tetrahydrothiopyranyl | H | H | H | EP-A 38 38 309 |
| 12.46 | $n-C_3H_7$ | $CH_2$-(5-chloro-2-thienyl) | tetrahydrothiopyranyl | H | H | H | EP-A 177 913 |
| 12.47 | $C_2H_5$ | $CH_2$-(5-chloro-2-thienyl) | tetrahydrothiopyranyl | H | H | H | EP-A 177 913 |
| 12.48 | $C_2H_5$ | $CH_2$-(5-chloro-2-thienyl) | tetrahydropyranyl | H | H | H | EP-A 177 913 |
| 12.49 | $n-C_3H_7$ | $CH_2$-(5-chloro-2-thienyl) | tetrahydropyranyl | H | H | H | EP-A 177 913 |

TABLE 12-continued

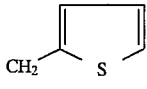

XI

| No. | $R^d$ | $R^e$ | $R^f$ | $R^g$ | $R^h$ | $R^i$ | Reference |
|---|---|---|---|---|---|---|---|
| 12.50 | n-$C_3H_7$ | $CH_2$-thienyl | tetrahydrothiopyranyl | H | H | H | EP-A 177 913 |
| 12.51 | $CH_3$ | $CH_2$-thienyl | tetrahydropyranyl | H | H | H | EP-A 177 913 |
| 12.52 | $C_2H_5$ | $CH_2$-thienyl | tetrahydropyranyl | H | H | H | EP-A 177 913 |

TABLE 13

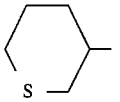

XI ($R^e = -CH_2(CH_2)_2CH_2-$phenyl with Radicals ; $R^g, R^h, R^i = H$)

| No. | $R^d$ | $R^f$ | Radicals on phenyl ring | phys. data [NMR* ($\delta$ in ppm)] |
|---|---|---|---|---|
| 13.01 | $C_2H_5$ | tetrahydropyranyl | 4-F | 2.9 (broad, 2H); 4.1 (broad, 2H) |
| 13.02 | n-$C_3H_7$ | tetrahydropyranyl | 4-F | 2.9 (t, 2H); 4.05 (broad, 2H) |
| 13.03 | $C_2H_5$ | tetrahydrothiopyranyl | 4-F | 2.9 (t, 2H); 4.05 (broad, 2H) |
| 13.04 | n-$C_3H_7$ | tetrahydrothiopyranyl | 4-F | 2.9 (t, 2H); 4.05 (broad, 2H) |
| 13.05 | $C_2H_5$ | tetrahydropyranyl | 4-F | 4.05 (broad, 2H) |

TABLE 13-continued

Radicals XI

[Structure: cyclohexenone with OH, R^f substituent, =N-O-CH2(CH2)2CH2-phenyl with Radicals, and R^d substituent]

(R^e = —CH2(CH2)2CH2—phenyl with Radicals ; R^g, R^h, R^i = H)

| No. | R^d | R^f | Radicals on phenyl ring | phys. data [NMR* (δ in ppm)] |
|---|---|---|---|---|
| 13.06 | n-C3H7 | tetrahydropyran-4-yl (O) | 4-F | 4.05 (broad, 2H) |
| 13.07 | C2H5 | tetrahydropyran-4-yl (O) | 4-Cl | 2.9 (t, 2H); 4.05 (broad, 2H) |
| 13.08 | n-C3H7 | tetrahydropyran-4-yl (O) | 4-Cl | 2.9 (t, 2H); 4.05 (broad, 2H) |
| 13.09 | C2H5 | tetrahydropyran-4-yl (O) | 4-Cl | 2.9 (t, 2H); 4.05 (broad, 2H) |
| 13.10 | n-C3H7 | tetrahydropyran-4-yl (O) | 4-Cl | 2.9 (broad, 2H); 4.05 (broad, 2H) |
| 13.11 | C2H5 | tetrahydrothiopyran-4-yl (S) | 4-Cl | 4.05 (broad, 2H) |
| 13.12 | n-C3H7 | tetrahydrothiopyran-4-yl (S) | 4-Cl | 4.05 (broad, 2H) |

*) selected signals

Herbicidal active ingredients and antidote compounds can be applied together or separately, after emergence, to the leaves and shoots of the crops and of the undesirable grasses. The antidote is preferably applied simultaneously with the herbicidal active ingredient. Separate application, where the antidote is first applied to the field, followed by the herbicidal active ingredient, is also possible. The herbicidal active ingredient and the antidote can be formulated together or separately as a spray in suspendable, emulsifiable or soluble form.

Antidote effects are also achieved by treating the seeds of crop plants or the seedlings with the antidote before sowing or before planting out. The herbicidal active ingredient is then applied alone in the conventional manner.

In the treatment of seeds, in general amounts of active ingredient of from 0.1 to 10 g, preferably from 1 to 2 g, per kilogram of seed are required.

In the application of the antidote by seed swelling or in the treatment of seedlings, solutions which contain the antagonistic active ingredient in a concentration of from 1 to 10,000 ppm, in particular from 100 to 10,000 ppm, are preferably used.

For herbicidal (hetaryloxy)- or aryloxyphenoxyacetic acid derivatives X, different amounts of an antidote compound are required if the herbicide is used in different crops. The ratios can be varied within wide ranges. They are also dependent on the structure of (hetaryloxy)- or aryloxyphenoxyacetic acid derivatives and on the particular target crop. Suitable weight ratios of herbicidal active ingredient to antidote compound are from 1:10 to 1:0.01, preferably from 1:4 to 1:0.1.

Different amounts of an antidote compound are required for the same cyclohexenone derivative XI if the latter is used in different crops. The ratios in which a cyclohexenone derivative and a substituted 5-aminopyrazole I or I' are used can be varied within wide limits. They are dependent on the structure of the cyclohexenone derivative and of the substituted 5-aminopyrazole I or I' and on the particular crop. Suitable weight ratios of herbicidal active ingredient to antidote compound are from 1:10 to 1:0.01, preferably from 1:4 to 1:0.25.

The novel agents or, in the case of separate application, the herbicidal active ingredients and the antidote are applied, for example, in the form of directly sprayable solutions, powders, suspensions, including concentrated aqueous, oily or other suspensions, or dispersions, emulsions, oil dispersions, pastes, dusting agents, broadcasting agents or granules, by spraying, atomizing, dusting, broadcasting or pouring. The application forms depend entirely on the intended uses.

For the preparation of directly sprayable solutions, emulsions, pastes and oil dispersions, mineral oil fractions of medium to high boiling point, such as kerosene or diesel oil, such as coal tar oils and oils of vegetable or animal origin, aliphatic, cyclic or aromatic hydrocarbons, eg. benzene, toluene, xylene, paraffin, tetrahydronaphthalene, alkylated naphthalenes or derivatives thereof, for example methanol, ethanol, propanol, butanol, chloroform, carbon tetrachloride, cyclohexanol, cyclohexanone, chlorobenzene or isophorone, or strongly polar solvents, such as dimethylformamide, dimethyl sulfoxide, N-methylpyrrolidone and water, are suitable.

Aqueous application forms can be prepared from emulsion concentrates, pastes, wettable powders or oil dispersions by adding water. For the preparation of emulsions, pastes or oil dispersions, the herbicidal active ingredient and/or the antidote, as such or in solution in an oil or solvent, can be homogenized in water by means of wetting agents, adherents, dispersants or emulsifiers. However, it is also possible to prepare concentrates which consist of the herbicidal active ingredient and/or the antidote and wetting agents, adherents, dispersants or emulsifiers or possibly solvents or oil and which are suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensates of sulfonated naphthalene and naphthalene derivatives with formaldehyde, condensates of naphthalene or of naphthalenesulfonic acids with phenol and formaldehyde, polyoxyethylene octylethene ethers, ethoxylated isooctylphenol- [sic], octylphenol and nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the herbicidal active ingredient and/or the antidote together with a solid carrier.

Granules, for example coated, impregnated and homogeneous granules, can be prepared by binding the active ingredients to solid carriers. Examples of solid carriers are mineral earths, such as silica gel, silicas, silica gels, silicates, talc, kaolin, attaclay, limestone, chalk, talc, bole, loess, clay, dolomite, kieselguhr, calcium sulfate, magnesium sulfate, magnesium oxide, milled plastics, fertilizers, eg. ammonium sulfate, ammonium phosphate, ammonium nitrate and ureas, and vegetable products, such as grain flours, bark meal, wood meal and nutshell meal, cellulosic powders and other solid carriers.

The formulations contain from 0.01 to 95, preferably from 0.5 to 90%, by weight of herbicidal active ingredient and antidote. The application rates of herbicidal active ingredient are from 0.2 to 5 kg of active substance (a.s.) per hectare.

In addition to the substituted 5-aminopyrazole I or I' as the antidote and the herbicide from the group consisting of the (hetaryloxy)- or aryloxyphenoxyacetic acids X or of the cyclohexenones XI, the novel herbicides may contain further herbicidal or growth-regulating active ingredients having a different chemical structure, the antagonistic effect being retained.

EXAMPLE 1

1-Phenyl-4-cyano-5-(n-propylcarbonylamino)-pyrazole

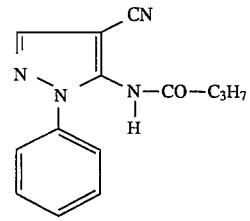

6.8 ml (66 mmol) of butyryl chloride were added to a solution of 5.52 g (30 mmol) of 1-phenyl-4-cyano-5-aminopyrazole [known from J. Org. Chem. 21 (1956), 1240] in 70 ml of pyridine. The mixture was heated for 15 hours at 50° C. and then poured into 500 ml of 5% strength by weight aqueous hydrochloric acid. The product was extracted from the aqueous phase with methylene chloride and then isolated in a conventional manner. Yield: 50%.

EXAMPLE 2

1-Phenyl-4-cyano-5-(phenylureido)-pyrazole

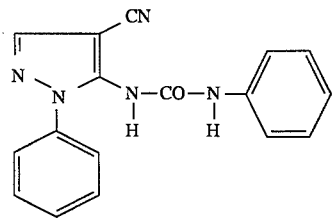

9.0 g (80 mmol) of potassium tert-butylate and 8.7 ml (80 mmol) of phenyl isocyanate were added to a solution of 5.52 g (30 mmol) of 1-phenyl-4-cyano-5-aminopyrazole in 100 ml of toluene. The mixture was heated for 15 hours at 80° C. and then cooled, the insoluble constituents were separated off and the resulting solution was acidified with acetic acid, the product crystallizing out. Yield: 96%.

EXAMPLE 3

1-Phenyl-4-cyano-5-(dicyclohexylaminosulfonylureido)pyrazole

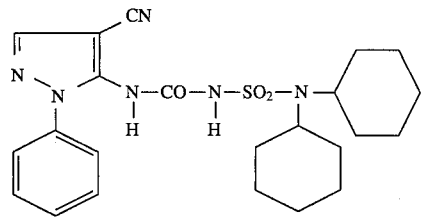

4.4 ml (50 mmol) of chlorosulfonyl isocyanate were added to a solution of 9.2 g (50 mmol) of 1-phenyl-4-cyano-5-aminopyrazole in 100 ml of methylene chloride. Stirring was carried out for 30 minutes at about 20° C., after which a solution of 7.5 ml (60 mmol) of triethylamine and 10 ml (50 mmol) of dicyclohexylamine in 50 ml of methylene chloride was slowly added dropwise. After the end of the addition, stirring was continued for a further hour and hydrolysis was then carried out with 200 ml of water. The organic phase was separated off and was worked up in a conventional manner to give the product. Yield: 87%.

EXAMPLE 4

4-Cyano-1-phenyl-5-(N-phthalimido)-pyrazole

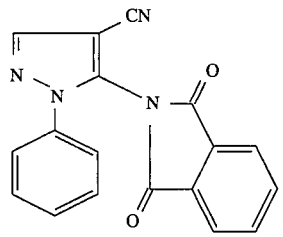

A mixture of 9.2 g (0.05 mol) of 1-phenyl- 4-cyano-5-aminopyrazole, 14.8 g (0.1 mol) of phthalic anhydride and 100 ml of glacial acetic acid was refluxed for 4 hours, cooled to 25° C. and then diluted with 200 ml of water. The pH was then brought to 10 with 300 ml of 25% strength by weight aqueous sodium hydroxide solution, and the solid product was then separated off. Yield: 62%.

EXAMPLE 5

4-Cyano-1-methyl-5-(p-chlorobenzoylthioureido)-pyrazole

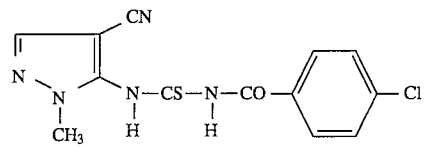

6.4 ml (50 mmol) of p-chlorobenzoyl chloride were added to a solution of 4.2 g (55 mmol) of ammonium isothiocyanate in 100 ml of acetone at about 20° C. Stirring was carried out for 30 minutes, after which a solution of 6.1 g (50 mmol) of 5-amino-4-cyano-1-methylpyrazole in 100 ml of acetone was slowly added dropwise at 50° C. This mixture was heated at the boil for 4 hours, cooled to about 25° C. and then diluted with 1000 ml of water. The product was extracted with ethyl acetate. Yield: 65%.

The physical data of the end points [sic] I are shown in Table 14 below, which also lists further compounds I which were prepared, or can be prepared, by the same methods.

Table 15 summarizes the known compounds of type I', which, in addition to the compounds I, are preferred antidotes.

TABLE 14

I ($R^2 = H$; $R^3 = CN$)

| Exp. No. | $R^1$ | $R^4$ | $R^5$ | mp. [°C.] |
|---|---|---|---|---|
| 14.001 | | | | |
| 14.002 | $C_6H_5$ | $CO-CH_2-CH_3$ | H | |
| 14.003 | $C_6H_5$ | $CO-CH_2-CH_2-CH_3$ | H | 82–83 |
| 14.004 | $C_6H_5$ | $CO-(CH_2)_6-CH_3$ | H | |
| 14.005 | $C_6H_5$ | $CO-(CH_2)_{14}-CH_3$ | H | 72–76 |
| 14.006 | $C_6H_5$ | $CO-C(CH_3)_3$ | H | 163–168 |
| 14.007 | $C_6H_5$ | $CO-CH_2-C(CH_3)_3$ | H | |
| 14.008 | $C_6H_5$ | $CO-CH_2-Cl$ | H | |
| 14.009 | $C_6H_5$ | $CO-CH_2-CH_2-Cl$ | H | 124–130 |
| 14.010 | $C_6H_5$ | $CO-CH_2-CH_2-CH_2-Cl$ | H | 102–106 |
| 14.011 | $C_6H_5$ | $CO-CCl_3$ | H | |
| 14.012 | $C_6H_5$ | $CO-CF_3$ | H | 129–132 |
| 14.013 | $C_6H_5$ | $CO-C_6H_5$ | H | |
| 14.014 | $C_6H_5$ | $CO-(4-CH_3-C_6H_4)$ | H | |
| 14.015 | $C_6H_5$ | $CO-(2-Cl-C_6H_4)$ | H | |
| 14.016 | $C_6H_5$ | $CO-(4-Cl-C_6H_4)$ | H | |
| 14.017 | $C_6H_5$ | $CO-(2,4-Cl_2-C_6H_3)$ | H | |

TABLE 14-continued

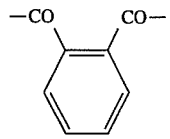

($R^2 = H$; $R^3 = CN$) I

| Exp. No. | $R^1$ | $R^4$ | $R^5$ | mp. [°C.] |
|---|---|---|---|---|
| 14.018 | $C_6H_5$ | $CO-(2-NO_2-C_6H_4)$ | H | |
| 14.019 | $C_6H_5$ | $CO-(3-NO_2-C_6H_4)$ | H | |
| 14.020 | $C_6H_5$ | $CO-(4-NO_2-C_6H_4)$ | H | 205–209 |
| 14.021 | $C_6H_5$ | $SO_2-CH_3$ | H | 132–136 |
| 14.022 | $C_6H_5$ | $SO_2-C_6H_5$ | H | 118–126 |
| 14.023 | $C_6H_5$ | $SO_2-(4-Cl-C_6H_4)$ | H | 190–193 |
| 14.024 | $C_6H_5$ | $CO-NH-CH_3$ | H | |
| 14.025 | $C_6H_5$ | $CO-NH-(CH_2)_3-CH_3$ | H | |
| 14.026 | $C_6H_5$ | $CO-NH-C_6H_5$ | H | 156–157 |
| 14.027 | $C_6H_5$ | $CO-NH-(3,4-Cl_2-C_6H_3$ | H | |
| 14.028 | $C_6H_5$ | $CS-NH-C_6H_5$ | H | 110–111 |
| 14.029 | $C_6H_5$ | $CO-NH-SO_2-NH-C_6H_{11}$ | H | 115 (decomp). |
| 14.030 | $C_6H_5$ | $CO-NH-SO_2-N(C_6H_{11})_2$ | H | 115 (decomp). |
| 14.031 | $C_6H_5$ | $CO-NH-SO_2-NH-C_6H_5$ | H | 110 (decomp). |
| 14.032 | $C_6H_5$ | $CO-CH_3$ | $CO-CH_3$ | 112–113 |
| 14.033 | $C_6H_5$ | $CO-CH_2-CH_3$ | $CO-CH_2-CH_3$ | 78–84 |
| 14.034 | $C_6H_5$ | $CO-CH_2-C(CH_3)_3$ | $CO-CH_2-C(CH_3)_3$ | 89–92 |
| 14.035 | $C_6H_5$ | $CO-(2,4-Cl_2-C_6H_3)$ | $CO-(2,4-Cl_2-C_6H_3)$ | 146–148 |
| 14.036 | $C_6H_5$ | $CO-(2-NO_2-C_6H_4)$ | $CO-(2-NO_2-C_6H_4)$ | 184–194 |
| 14.037 | | —CO—⌬—CO— | | 183–190 |
| 14.038 | $C_6H_5$ | $SO_2-(4-CH_3-C_6H_4)$ | $SO_2-(4-CH_3-C_6H_4)$ | 155–156 |
| 14.039 | $C_6H_5$ | $SO_2-(4-Cl-C_6H_4)$ | $SO_2-(4-Cl-C_6H_4)$ | 190–193 |
| 14.040 | $C_6H_5$ | Co-Cyclopropyl | H | 143–145 |
| 14.041 | $C_6H_5$ | $CO-CH_2-C_6H_5$ | H | 142–144 |
| 14.042 | $C_6H_5$ | $CO-CH_2-CH_2-C_6H_5$ | H | 128–130 |
| 14.043 | $C_6H_5$ | $=CH-C_6H_5$ | | 87–93 |
| 14.044 | $C_6H_5$ | $=CH-(4-Cl-C_6H_4)$ | | 126–129 |
| 14.045 | $C_6H_5$ | $=CH-(2-Cl-C_6H_4)$ | | 128–130 |
| 14.046 | $CH_3$ | $CO-CH_2-CH_3$ | H | |
| 14.047 | $CH_3$ | $CO-CH_2-CH_2-CH_3$ | H | 86–90 |
| 14.048 | $CH_3$ | $CO-(CH_2)_6-CH_3$ | H | |
| 14.049 | $CH_3$ | $CO-(CH_2)_{14}-CH_3$ | H | 92–94 |
| 14.050 | $CH_3$ | $CO-C(CH_3)_3$ | H | 129–131 |
| 14.051 | $CH_3$ | $CO-CH_2-C(CH_3)_3$ | H | 103–104 |
| 14.052 | $CH_3$ | $CO-CH_2-CH_2-Cl$ | H | |
| 14.053 | $CH_3$ | $CO-CH_2-CH_2-CH_2-Cl$ | H | oil |
| 14.054 | $CH_3$ | $CO-CCl_3$ | H | |
| 14.055 | $CH_3$ | $CO-CF_3$ | H | |
| 14.056 | $CH_3$ | $CO-(4-CH_3-C_6H_4)$ | H | |
| 14.057 | $CH_3$ | $CO-(2-Cl-C_6H_4)$ | H | |
| 14.058 | $CH_3$ | $CO-(2,4-Cl_2-C_6H_3)$ | H | 193–194 |
| 14.059 | $CH_3$ | $CO-(2-NO_2-C_6H_4)$ | H | 222–226 |
| 14.060 | $CH_3$ | $CO-(3-NO_2-C_6H_4)$ | H | |
| 14.061 | $CH_3$ | $CO-(4-NO_2-C_6H_4)$ | H | 181–182 |
| 14.062 | $CH_3$ | $SO_2-CH_3$ | H | 120–123 |
| 14.063 | $CH_3$ | $SO_2-C_6H_5$ | H | 190–197 |
| 14.064 | $CH_3$ | $SO_2-(4-Cl-C_6H_4)$ | H | 209–210 |
| 14.065 | $CH_3$ | $CO-NH-CH_3$ | H | |
| 14.066 | $CH_3$ | $CO-NH-(CH_2)_3-CH_3$ | H | |
| 14.067 | $CH_3$ | $CO-NH-C_6H_5$ | H | |
| 14.068 | $CH_3$ | $CO-NH-(3,4-Cl_2-C_6H_3)$ | H | |
| 14.069 | $CH_3$ | $CS-NH-C_6H_5$ | H | |
| 14.070 | $CH_3$ | $CO-NH-SO_2-NH-C_6H_{11}$ | H | |
| 14.071 | $CH_3$ | $CO-NH-SO_2-N(C_6H_{11})_2$ | H | 100 (decomp.) |
| 14.072 | $CH_3$ | $CS-NH-CO-C_6H_5$ | H | 140 |
| 14.073 | $CH_3$ | $CS-NH-CO-(2-Cl-C_6H_4)$ | H | 168 |
| 14.074 | $CH_3$ | $CS-NH-CO-(4-Cl-C_6H_4)$ | H | 215–217 |
| 14.075 | $CH_3$ | $CS-NH-CO-(2-NO_2-C_6H_4)$ | H | 141 (decomp.) |
| 14.076 | $CH_3$ | $CS-NH-CO-(3-NO_2-C_6H_4)$ | H | 144–148 |
| 14.077 | $CH_3$ | $CS-NH-CO-(4-NO_2-C_6H_4)$ | H | >240 |
| 14.078 | $CH_3$ | $CO-C(CH_3)_3$ | $CO-C(CH_3)_3$ | 111–113 |

TABLE 14-continued

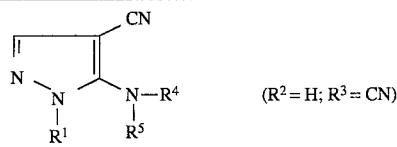

($R^2 = H$; $R^3 = CN$)

| Exp. No. | $R^1$ | $R^4$ | $R^5$ | mp. [°C.] |
|---|---|---|---|---|
| 14.079 | $CH_3$ | $SO_2-(4-CH_3-C_6H_4)$ | $SO_2-(4-CH_3-C_6H_4)$ | 176–180 |
| 14.080 | $CH_3$ | $SO_2-C_6H_5$ | $SO_2-C_6H_5$ | 190–197 |
| 14.081 | $CH_3$ | CO-Cyclopropyl | H | 170–173 |
| 14.082 | $CH_3$ | $CO-CH_2-C_6H_5$ | H | 122–125 |
| 14.083 | $CH_3$ | $CO-CH_2-CH_2-C_6H_5$ | H | 114–116 |
| 14.084 | $CH_3$ | $=CH-C_6H_5$ | | 113–115 |
| 14.085 | $CH_3$ | $=CH-(4-Cl-C_6H_4)$ | | 110–111 |
| 14.086 | $CH_3$ | $=CH-(2-Cl-C_6H_4)$ | | 145–147 |

TABLE 15

Known 5-aminopyrazoles I'

($R^2 = H$; $R^3 = CN$)

| Exp. No. | $R^1$ | $R^2$ | $R^4$ | mp. [°C.] | Ref. |
|---|---|---|---|---|---|
| 15.01 | $CH_3$ | H | H | 222–223 | 1/3 |
| 15.02 | $C_6H_5$ | H | H | 158–160 | 1/3 |
| 15.03 | $4-Cl-C_6H_5$ | H | H | 167–167.5 | 1/3 |
| 15.04 | $4-NO_2-C_6H_4$ | H | H | 224–225 | 1 |
| 15.05 | $CH_3$ | $CH_3$ | H | 194 | 1 |
| 15.06 | $C_6H_5$ | $CH_3$ | H | 132–133 | 1 |
| 15.07 | $C_6H_5$ | $CF_3$ | H | 115–116 | 2 |
| 15.08 | $4-NO_2-C_6H_5$ | $CF_3$ | H | 213–214 | 2 |
| 15.09 | H | $CH_3$ | H | 163 | 1 |
| 15.10 | $2,4-Cl_2-C_6H_3$ | H | H | 141–142 | 4 |
| 15.11 | $CH_2-CH_2OH$ | H | H | 158–160 | 1 |
| 15.12 | $4-Br-C_6H_4$ | H | H | 168–170 | 1 |
| 15.13 | $2-Cl-C_6H_4$ | H | H | 124 | 1 |
| 15.14 | $2-CH_3-C_6H_4$ | H | H | 158–159 | 1 |
| 15.15 | $C_6H_5$ | H | $CO-CH_3$ | 95–97 | |
| 15.16 | $CH_3$ | H | $CO-CH_3$ | 120–130 | |
| 15.17 | $CH_3$ | H | $CO-CH_2Cl$ | | |
| 15.18 | $CH_3$ | H | $CO-C_6H_5$ | 173–174 | |
| 15.19 | $CH_3$ | H | $CO-(4-Cl-C_6H_4)$ | | |
| 15.20 | $CH_3$ | H | CO-Cyclohexyl | 154–156 | |

References:

[1] K. Robins et al., J. Org. Chem. 21 (1956), 1240
[2] K. Tanaka et al., Bull. Chem. Soc. Jpn. 60 (1987), 4480
[3] R. J. Quinn et al., Aust. J. Chem. Soc. 42 (1989), 747
[4] P. L. Southwick et al., J. Heterocycl. Chem. 12 (1975), 1199

Examples of biological action

The effect of various novel herbicides or herbicide combinations consisting of the herbicide and the antidote compound on the growth of desired and undesirable plants in comparison with the herbicidal active ingredient alone is demonstrated by the following biological examples from greenhouse experiments:

In the greenhouse experiments, the culture vessels used were plastic flower pots having a capacity of about 300 cm³ and containing loamy sand with about 3.0% of humus as a substrate. The seeds of the test plants were sown shallowly and separately according to species and were moistened. Thereafter, the vessels were covered with transparent plastic covers until the seeds had uniformly germinated and the plants had begun to grow.

List of test plants

| Botanical name | Common name |
|---|---|
| Brachiaria platphylla | Broadleaf signalgrass |
| Triticum aestivum | Spring wheat |
| Zea mays | Indian corn |

For the postemergence treatment, the test plants are first grown cultivated to a height of 3 to 20 cm, depending on the form of growth, before being treated. The herbicides were suspended or emulsified in water as a distributing agent and sprayed by means of finely distributing nozzles.

The herbicide used as an example of the cyclohexenone derivative of the formula XI was

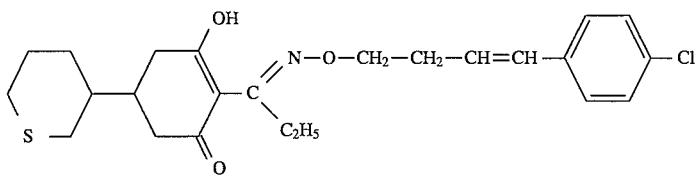

For the postemergence treatment, all antidote compounds were prepared in a mixture consisting of 80% by weight of cyclohexenone as solvent and 20% by weight of surfactant (Emulphor EL*) with 10% by weight of active ingredient.

*) Ethoxylated castor oil

For comparison, the herbicidal active ingredient 12.42 was formulated as a 10–20% by weight emulsion concentrate and was used in the spray liquor in each case with the addition of the amount of solvent system with which the antidote compound were applied at the application rates shown [lacuna] Tables. The solution was prepared by mixing the active ingredient into a solution of 93% by weight of xylene and 7% by weight of Lutensol® AP-8**).

**) Nonionic surfactant based on alkylphenol polyethylene glycol ethers

After application of the active ingredient mixtures, the test plants were cultivated in a greenhouse, warmth-loving species at about 18°–30° C. and those from more temperate climates at about 10°–25° C.

The test period extended over from 3 to 5 weeks. During this time, the plants were tended and their reaction to the individual treatments was recorded.

The damage caused by the chemical agents was evaluated on the basis of a scale from 0 to 100% in comparison with the untreated control plants. 0 means no damage and 100 means complete destruction of the plants.

Table 16 documents the antagonistic action of the novel example compounds No. 14.028, 14.058, 14.059 and 15.18.

TABLE 16

Improvement of the toleration of the herbicide 12.42 by corn as a result of admixing an antagonistic substituted 5-aminopyrazole during postemergence application:

| Anti-dote No. | Application rate [kg/ha a.s.] Herbicide Antidote | Greenhouse experiment | |
|---|---|---|---|
| | | Test plants and damage [%] | |
| | | Crop Zea mays[1)] | Undesirable plant Brachiaria platphylla |
| — | 0.06 | 40 | 90 |
| 5.18 | 0.06 + 0.06 | 10 | 80 |
| 4.058 | 0.06 + 0.06 | 20 | 100 |
| 4.059 | 0.06 + 0.06 | 15 | 80 |
| 4.028 | 0.06 + 0.06 | 20 | 75 |

[1)]Lixis variety

Table 16 shows that the substituted 5-aminopyrazoles increase the toleration of the herbicide 12.42 by crops from the Gramineae family (grasses).

We claim:

1. A substituted 5-aminopyrazole of the formula I

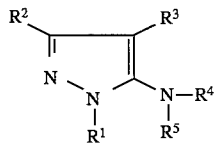

where $R^1$ is $C_1$–$C_8$-alkyl, $C_1$–$C_8$-hydroxyalkyl or a phenyl group which may carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio or —$NR^6R^7$, where $R^6$ and $R^7$ are each hydrogen or $C_1$–$C_4$-alkyl, and the phenyl group may additionally carry a number of halogen atoms so that the total number of radicals is 4 or 5;

$R^2$ is hydrogen or $C_1$–$C_4$-alkyl which may be unsubstituted or partially or completely halogenated;

$R^3$ is cyano or CO—$R^8$ or CS—$R^8$, where $R^8$ is hydroxyl, $C_1$–$C_4$-alkoxy, amino, $C_1$–$C_4$-alkylamino or di-$C_1$–$C_4$-alkylamino;

$R^4$ and $R^5$ are each hydrogen, $C_1$–$C_4$-alkyl, $PX(OR^9)_2$, $SO_2$—$R^9$, CX—$R^{10}$, CX—NH—CY—$R^9$ or CX—NH—$SO_2$—$R^{11}$, where X and Y are each oxygen or sulfur;

$R^9$ is one of the substituents $R^1$;

$R^{10}$ is $C_1$–$C_{20}$-alkyl, $C_1$–$C_4$-alkoxy or a phenyl group which may carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio or —$NR^6R^7$, and which may additionally carry a further number of halogen atoms so that the total number of radicals is 5; amino which may be unsubstituted or may carry a $C_1$–$C_4$-alkyl, cycloalkyl or phenyl radical, where the phenyl radical may additionally carry from one to three of the following radicals: halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio, and the phenyl group may additionally contain a further number of halogen atoms so that the total number of radicals is 4 or 5;

$R^{11}$ is amino, $C_1$–$C_4$-alkylamino, di-$C_1$–$C_4$-alkylamino, pyrrolidinyl, piperidinyl or morpholinyl;

or $R^4$ and $R^5$ together form a group =$CR^{12}R^{13}$ or —CO—W—CO—, where $R^{12}$ is hydrogen, amino, $C_1$–$C_4$-alkylamino or $C_3$—$C_8$-cycloalkylamino;

$R^{13}$ is amino, $C_1$–$C_4$-alkylamino, di-$C_1$–$C_4$-alkylamino, $C_3$–$C_8$-cycloalkylamino, pyrrolidin-1-yl, piperidin-1-yl, morpholin-4-yl, phenyl or pyridyl, where the two last-mentioned substituents may furthermore carry from one to three of the following radicals: halogen, nitro, $C_1$–$C_4$-alkyl, partially or completely halogenated $C_1$–$C_4$-alkyl, $C_1$–$C_4$-alkoxy, partially or completely halogenated $C_1$–$C_4$-alkoxy or $C_1$–$C_4$-alkylthio;

W is an ethylene or ethenylene bridge, a 5-membered or 6-membered 1,2-C-bonded aromatic or heteroaromatic bridge having a nitrogen, oxygen or sulfur atom as the hetero atom, where these bridge members may furthermore carry, on each substitutable carbon atom, a radical selected from up to 2 of the following: halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio and partially or completely halogenated $C_1$–$C_4$-alkylthio, and where the bridge members may additionally carry a number of halogen atoms equivalent to the number of further substitutable carbon atoms, or a 5-membered or 6-membered 1,2-C-bonded cycloalkylene or cycloalkenylene bridge, where these substituents may furthermore carry from one to four of the following radicals: halogen or $C_1$–$C_4$-alkyl;

and the basic salts of the compounds I in which $R^3$ is hydroxycarbonyl or hydroxythiocarbonyl, and the acidic salts of the compounds I which contain a basic nitrogen atom, with the exception of 1-phenyl- and 1-methyl-4-cyano-5-acylaminopyrazole, 1-methyl-4-cyano-5-(chloromethylcarbonylamino)-pyrazole, 1-methyl-4-cyano-5-(phenylcarbonylamino)-pyrazole, 1-methyl-4-cyano-5-(p-chlorophenylcarbonylamino)-pyrazole, 5-amino-4-cyano-1-methylpyrazole, 5-amino-4-cyano-1,3-dimethylpyrazole, 5-amino-4-cyano-1-methyl-3-trifluoromethylpyrazole, 5-amino-1,3-dimethylpyrazole-4-carboxamide, 5-amino-1-methylpyrazole-4-carboxamide, 5-amino-1-(2-hydroxyethyl)-pyrazole-4-carboxamide, 5-amino-4-cyano-1-(2-hydroxyethyl)-pyrazole and those compounds I in which either $R^1$ is unsubstituted or substituted phenyl and $R^4$ and $R^5$ are simultaneously hydrogen or $R^1$ is unsubstituted or substituted phenyl, $R^2$ and $R^5$ are each hydrogen, $R^3$ is cyano and $R^4$ is hydrogen or $C_1$–$C_4$-alkylamino or $R^1$ is substituted phenyl, $R^2$ and $R^5$ are each hydrogen,
$R^3$ is cyano, $C_1$–$C_4$-alkoxycarbonyl, aminocarbonyl or $C_1$–$C_4$-alkylaminocarbonyl and $R^4$ is CX—($C_1$–$C_4$-alkoxy), or substituted or unsubstituted CX—$NH_2$, and
with the exception of those compounds I in which one of the radicals $R^4$ or $R^5$ is $C_1$–$C_3$-alkyl and the other is methoxycarbonyl or ethoxycarbonyl when $R^2$ is hydrogen, $R^3$ is cyano and $R^1$ is substituted phenyl.

2. A substituted 5-aminopyrazole I as defined in claim 1, wherein $R^3$ is cyano.

3. A herbicidal composition containing one or more substituted 5-aminopyrazoles of the formula I', where I' corresponds to the definition of I without the exception, and one or more herbicidal active ingredients from the group consisting of
A) the 2-(4-hetaryloxy)- or 2-(4-aryloxy)-phenoxyacetic acid derivatives of the formula X

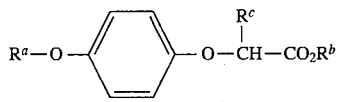

where
$R^a$ is phenyl, pyridyl, benzoxazyl, benzothiazyl or benzopyrazinyl, where these aromatic ring systems may carry up to two of the following radicals: halogen, nitro, $C_1$–$C_4$-alkyl, partially or completely halogenated $C_1$–$C_4$-alkyl or partially or completely halogenated $C_1$–$C_4$-alkoxy;
$R^b$ is hydrogen, $C_1$–$C_5$-alkyl, $C_3$–$C_5$-alkylideneimino, $C_3$–$C_5$-alkylideneiminoxy-$C_2$- or -$C_3$-alkyl or one equivalent of a plant-tolerated cation and
$R^c$ is hydrogen or methyl,
or
B) the cyclohexenone derivatives of the formula XI

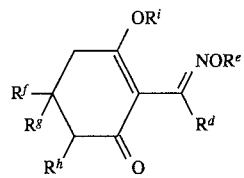

where
$R^d$ is $C_1$–$C_4$-alkyl;
$R^e$ is $C_1$–$C_4$-alkyl, $C_3$- or $C_4$-alkenyl, $C_3$- or $C_4$-alkynyl or partially or completely halogenated $C_3$- or $C_4$-alkenyl;
a $C_1$–$C_4$-alkylene or $C_2$–$C_4$-alkenyl chain, both of which may furthermore carry from 1 to 3 $C_1$–$C_3$-alkyl radicals and/or halogen atoms, or a 3-membered to 6-membered alkylene or 4-membered alkenylene chain which, if desired, is substituted by $C_1$–$C_3$-alkyl and each of which contains, as a chain member, an oxygen or sulfur atom which is not directly adjacent to the oxime ether moiety, all abovementioned chains carrying a terminal phenyl ring which in turn may be substituted by from one to three radicals selected from the group consisting of a benzyloxycarbonyl or phenyl radical and from one to three of each of the following radicals: nitro, cyano, halogen, $C_1$–$C_4$-alkyl, $C_1$–$C_4$-alkoxy, $C^1$–$C_4$-alkylthio, partially or completely hydrogenated $C_1$–$C_4$-alkyl, partially or completely halogenated $C^1$–$C_4$-alkoxy, carboxyl and $C_1$–$C_4$-alkoxycarbonyl, and it being possible for the phenyl ring additionally to carry a number of halogen atoms such that the total number of radicals is 4 or 5;
thienylmethyl which may furthermore carry a halogen atom;
$R^f$ is $C_1$–$C_4$-alkyl which may be monosubstituted by $C_1$–$C_4$-alkylthio or by $C_1$–$C_4$-alkoxy;

a 5-membered or 6-membered saturated or monounsaturated ring system which, in addition to carbon members, may contain an oxygen or sulfur atom or a sulfinyl or sulfonyl group, where this ring may carry up to three of the following radicals: hydroxyl, halogen, $C_1$–$C_4$-alkyl, partially or completely halogenated $C_1$–$C_4$-alkyl, $C_1$–$C_4$-alkoxy or $C_1$–$C_4$-alkylthio;
a 10-membered saturated or monounsaturated heterocyclic structure which contains two oxygen atoms or sulfur atoms and may be substituted by up to three $C_1$–$C_4$-alkyl groups and/or methoxy groups;
phenyl or pyridyl, where these groups may, if desired, carry up to three radicals selected from the group consisting of: $C_1$–$C_4$-alkyl, partially or completely halogenated $C_1$–$C_4$-alkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and benzoylamino;
pyrrolyl, pyrazolyl, thiazolyl or isoxazolyl, each of which may carry a $C_1$–$C_4$-alkyl group;
$R^g$ is hydrogen or hydroxyl or, when $R^f$ is $C_1$–$C_6$-alkyl, is $C_1$–$C_6$-alkyl;
$R^h$ is hydrogen, cyano, halogen, $C_1$–$C_4$-alkoxycarbonyl or a group

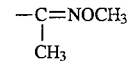

and
$R^i$ is hydrogen or one equivalent of an environmentally compatible cation.

4. A herbicidal composition as claimed in claim 3, containing a substituted 5-aminopyrazole I' and a herbicide X or a herbicide XI in a weight ratio of from 0.01:1 to 10:1.

5. A method for selectively controlling undesirable plant growth, wherein a substituted 5-aminopyrazole I' and
A) a 2-(4-hetaryloxy)- or 2-(4-aryloxy)-phenoxyacetic acid derivative of the formula X or
B) a cyclohexenone derivative of the formula XI as defined in claim 3 are applied simultaneously or in succession, during or after sowing of the crops or before or during emergence of the crops.

6. A method for selectively controlling undesirable plant growth, wherein the leaves of the crops and of the undesirable plants are treated simultaneously or in succession, by the postemergence method, with a substituted 5-aminopyrazole I' and
A) with a 2-(4-hetaryloxy)- or 2-(4-aryloxy)-phenoxyacetic acid derivative of the formula X or
B) with a cyclohexenone derivative of the formula XI as defined in claim 3.

7. A method for preventing damage to crops
A) by herbicidal 2-(4-hetaryloxy)- or 2-(4-aryloxy)-phenoxyacetic acid derivatives of the formula X or
B) by herbicidal cyclohexenone derivatives of the formula XI as defined in claim 3,
wherein the seed of the crops is treated with an antagonistic amount of substituted 5-aminopyrazole of the formula I', where I' corresponds to the definition of I without the exception.

8. A method as defined in claim 5, wherein the crops are barley, wheat, corn, sorghum and rice.

9. A process as defined in claim 6, wherein the crops are barley, wheat, cron, sorghum and rice.

10. A process as defined in claim 7, wherein the crops are barley, wheat, corn, sorghum and rice.

* * * * *

UNITED STATES PATENT AND TRADEMARK OFFICE
CERTIFICATE OF CORRECTION

PATENT NO.: 5,486,618

DATED: January 23, 1996

INVENTOR(S): HAGEN et al.

It is certified that error appears in the above-identified patent and that said Letters Patent is hereby corrected as shown below:

Column 59, claim 3, line 59, "$C^1$-$C_4$-alkoxy" should be --$C_1$-$C_4$-alkoxy--.

Signed and Sealed this

Eleventh Day of June, 1996

Attest:

BRUCE LEHMAN

Attesting Officer

Commissioner of Patents and Trademarks